(12) United States Patent
Drisko et al.

(10) Patent No.: US 12,339,870 B2
(45) Date of Patent: Jun. 24, 2025

(54) SYSTEMS AND METHODS FOR DATA CONVERSION

(71) Applicant: Zengines, Inc., Bedford, MA (US)

(72) Inventors: Richard Carl Drisko, Bedford, MA (US); Caitlyn Truong, Elmhurst, IL (US); Thomas P. Regan, Dunwoody, GA (US); Caroline Esther Jesurum, Needham, MA (US); Barrett Abernethy, Hungerford (GB)

(73) Assignee: Zengines, Inc., Bedford, MA (US)

( * ) Notice: Subject to any disclaimer, the term of this patent is extended or adjusted under 35 U.S.C. 154(b) by 0 days.

(21) Appl. No.: 18/835,540

(22) PCT Filed: Apr. 20, 2023

(86) PCT No.: PCT/US2023/019185
§ 371 (c)(1),
(2) Date: Aug. 2, 2024

(87) PCT Pub. No.: WO2023/205290
PCT Pub. Date: Oct. 26, 2023

(65) Prior Publication Data
US 2025/0117394 A1 Apr. 10, 2025

Related U.S. Application Data

(60) Provisional application No. 63/332,862, filed on Apr. 20, 2022.

(51) Int. Cl.
*G06F 16/25* (2019.01)
*G06F 16/21* (2019.01)

(52) U.S. Cl.
CPC .......... *G06F 16/258* (2019.01); *G06F 16/213* (2019.01)

(58) Field of Classification Search
CPC ............................. G06F 16/258; G06F 16/213
See application file for complete search history.

(56) References Cited

U.S. PATENT DOCUMENTS

| | | | |
|---|---|---|---|
| 11,556,593 B1 | 1/2023 | Gschwind et al. | |
| 2008/0015842 A1 | 1/2008 | Moore | |
| 2017/0169015 A1* | 6/2017 | Huang | G06F 40/51 |
| 2019/0205761 A1 | 7/2019 | Wu et al. | |
| 2022/0107711 A1* | 4/2022 | Tomokuni | H04N 1/00212 |

OTHER PUBLICATIONS

International Search Report and Written Opinion for PCT/US2023/019185 mailed Jul. 21, 2023 (7 pages).

* cited by examiner

*Primary Examiner* — Dangelino N Gortayo

(57) ABSTRACT

Systems and methods for data conversion from a source system to a target system. In some embodiments, the source system may comprise a plurality of source data structures, and the target system may comprise a target data structure. For each source data structure, a respective conversion score may be computed between the source data structure and the target data structure. The target data structure may be matched, based on the conversion scores, to a source data structure of the plurality of source data structures.

57 Claims, 14 Drawing Sheets

| Term | Context | Description | Data Type | Data Size | Related Term \| Relationship Type | Related Term \| Relationship Type | ... |
|---|---|---|---|---|---|---|---|
| ... | | | | | | | |
| Inv | IM | ... | ... | ... | Inventories \| Abbreviation | Inventory \| Abbreviation | ... |
| ... | | | | | | | |
| Inventory | ALL | ... | ... | ... | Inventories \| Singularization | Inv \| Expansion | ... |

FIG. 2

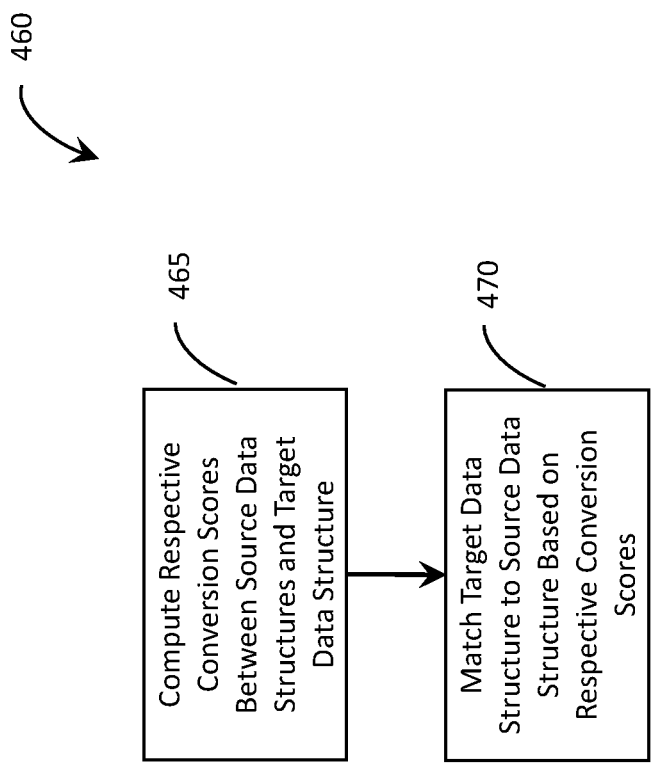

| Policy |
|---|
| Pol_No (primary key) |
| ... |
| Custom_Text1 |
| ... |
| Custom_Code1 |
| ... |

FIG. 4D

| Term | Context | Description | Data Type | Data Size | Related Term \| Relationship Type | Related Term \| Relationship Type | ... |
|---|---|---|---|---|---|---|---|
| ... | | | | | | | |
| Policy_ Custom _Text1 | Org. X | ... | ... | ... | Policy Name \| Alias | ... | |
| ... | | | | | | | |
| Policy_ Custom _Text1 | Org. Y | ... | ... | ... | Issuer Name \| Alias | ... | |

FIG. 4E

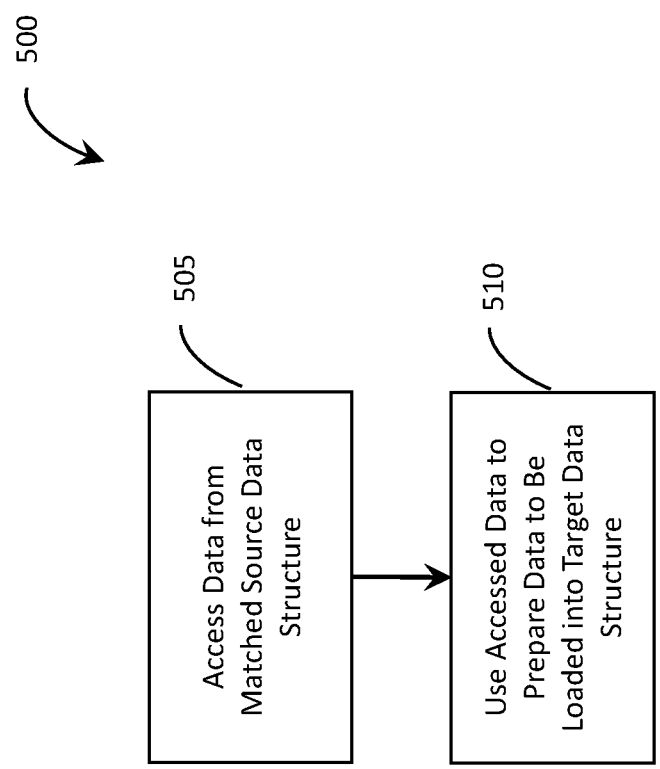

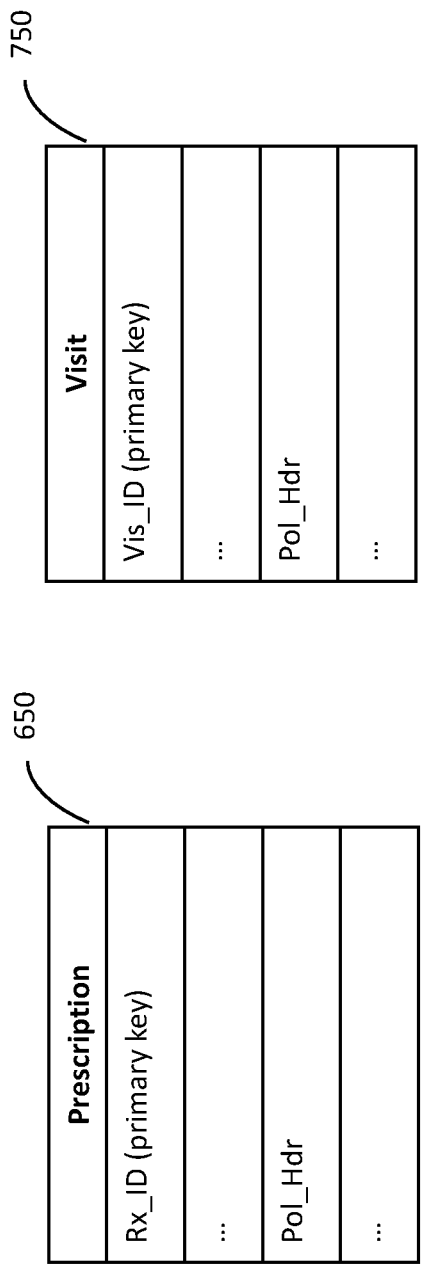

SYSTEMS AND METHODS FOR DATA CONVERSION

RELATED APPLICATION

This application is a U.S. national stage application, filed under 35 U.S.C. § 371, of International Application No. PCT/US2023/019185, filed on Apr. 20, 2023, which claims the benefit under 35 U.S.C. 119(e) of U.S. Provisional Patent Application No. 63/332,862, entitled "SYSTEMS AND METHODS FOR DATA CONVERSION," filed on Apr. 20, 2022, each of which is incorporated herein by reference in its entirety.

BACKGROUND

Digital transformation has accelerated over the past decade in important industries such as manufacturing, logistics, healthcare, finance, etc. Many organizations have transitioned from paper-based records to electronic records, and have used digital technologies to enhance both internal and external processes. Some organizations have also migrated from on-premises computing systems to cloud-based computing systems, for improved efficiency and reliability.

SUMMARY

In accordance with some embodiments, a computer-implemented method is provided for data conversion from a source system to a target system, the source system comprising a plurality of source data structures, the target system comprising a target data structure. The method comprises acts of: for each source data structure of the plurality of source data structures, computing a respective conversion score between the source data structure and the target data structure; and matching, based on the conversion scores, the target data structure to a source data structure of the plurality of source data structures.

In accordance with some embodiments, a system is provided, comprising at least one processor and at least one computer-readable storage medium having stored thereon instructions which, when executed, program the at least one processor to perform any of the methods described herein.

In accordance with some embodiments, at least one computer-readable storage medium is provided, having stored thereon instructions which, when executed, program at least one processor to perform any of the methods described herein.

BRIEF DESCRIPTION OF DRAWINGS

FIG. 2 shows an illustrative data dictionary 200, in accordance with some embodiments.

FIG. 4C shows an illustrative process 460 for matching a target data structure to a source data structure, in accordance with some embodiments.

FIG. 4D shows an illustrative data table 480, in accordance with some embodiments.

FIG. 4E shows the illustrative data dictionary 200 in the example of FIG. 2, with additional entries for aliases, in accordance with some embodiments.

FIG. 5 shows an illustrative process 500 for converting data from a source data structure into data to be loaded into a target data structure, in accordance with some embodiments.

FIG. 6B shows an illustrative data table 650, in accordance with some embodiments.

FIG. 7B shows an illustrative data table 750, in accordance with some embodiments.

DETAILED DESCRIPTION

Figure 1:
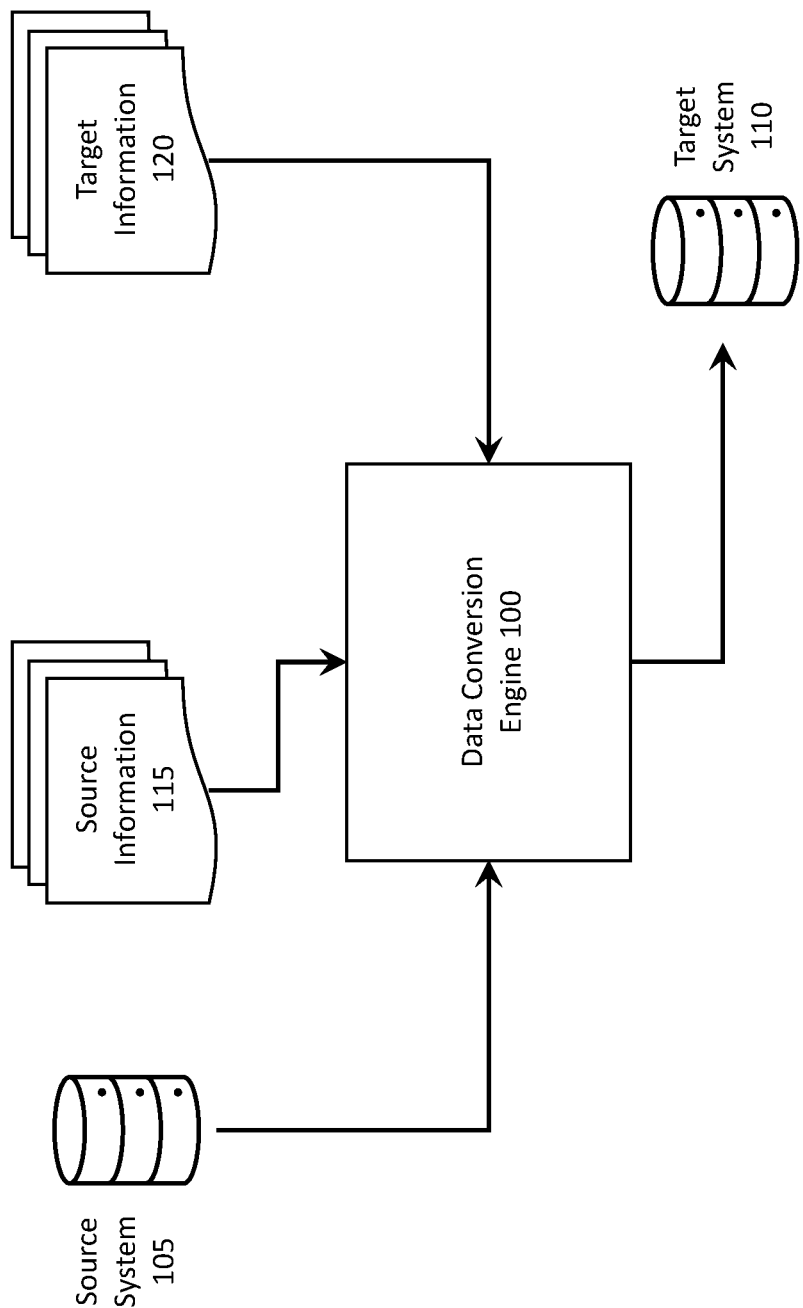
FIG. 1 shows an illustrative data conversion engine 100, in accordance with some embodiments.

Aspects of the present disclosure relate to systems and methods for data conversion. For instance, systems and methods are provided for facilitating a migration from one information management system to another.

The inventors have recognized and appreciated that, despite the significant progress that has been made in digital transformation, system migration remains a labor-intensive process. For instance, while a new information management system may be designed to manage similar data as an existing information management system, the two systems may use different schemas to organize the data (e.g., different sets of data tables connected in different ways). As a result, it may be challenging to populate the target system based on what is stored in the source system. For instance, it may be challenging to determine what data to retrieve from the source system, and whether/how to transform such data prior to loading into the target system.

Indeed, data fields in a target system are often manually matched to those in a source system, and any necessary data transformation may be manually programmed. This may require extensive knowledge over a particular application domain (e.g., manufacturing, logistics, healthcare, finance, etc.), as well as familiarity with inner workings of both the source system and the target system. In some instances, even with such subject matter expertise, the manual data conversion process may be slow, costly, and error prone.

The inventors have recognized and appreciated that the above-described challenges may impede progress in digital transformation. For instance, short-term obstacles presented by data conversion may discourage an organization from adopting new technologies, despite clear long-term benefits over legacy technologies. Accordingly, in some embodiments, techniques are provided for facilitating data conversion.

As an example, the inventors have recognized and appreciated that it may be beneficial to accumulate knowledge about how data is described, represented, and/or organized. Accordingly, in some embodiments, a data dictionary may be maintained, where each dictionary entry may be associated with a term, and may provide a natural language description, a data type, a data size, and/or other information for the term. Such entries may be built in any suitable manner, for example, based on available glossaries, information management systems previously encountered, etc.

The inventors have further recognized and appreciated that, in some instances, terms that are syntactically different may have the same meaning, or related meanings. For instance, "Healthcare Provider" may be generic to "Primary Care Physician," "Nurse Practitioner," etc. Accordingly, in some embodiments, an entry in a data dictionary may be related to one or more other entries, and a relationship type may be indicated for each related entry.

The inventors have further recognized and appreciated that some knowledge about data may be specific to a certain industry. For instance, in a healthcare context, PCP may be an acronym for "Primary Care Physician," whereas, in a finance context, PCP may be an acronym for "Previous Corresponding Period." Accordingly, in some embodiments, an entry in a data dictionary may indicate a context in which the entry is applicable.

As another example, the inventors have recognized and appreciated that, to facilitate data conversion, it may be beneficial to classify data tables and/or data fields. Any one or more suitable classification techniques may be used, such as supervised and/or unsupervised machine learning techniques. For instance, in some embodiments, one or more features may be determined for a data field, such as name, description, data type, data size, one or more relationships with other data fields, etc. Training data comprising feature vectors of labeled data fields may be used to train one or more classification models, which may include a neural network model, a decision tree model, an ensemble learning model, etc. A classification model is also referred to herein as a classifier.

Additionally, or alternatively, one or more clustering techniques may be used to analyze feature vectors of unlabeled data fields, to detect potential patterns. A detected pattern may then be used by a classifier to label data fields.

In some embodiments, data tables may be classified in a similar manner as data fields. For instance, one or more features may be determined for a data table, such as name, description, one or more features of data fields in the table (e.g., name, description, data type, data size, one or more relationships with other data fields, etc.), one or more connections to other data tables, etc.

As another example, the inventors have recognized and appreciated that, to facilitate data conversion, it may be beneficial to measure similarity between data fields. Accordingly, in some embodiments, a conversion score between two data fields may be computed based on respective feature vectors. Any suitable one or more features may be used, such as name, description, data type, data size, one or more classifications, one or more relationships with other data fields, etc.

In some embodiments, features of data fields may be weighted for purposes of computing conversion scores. For instance, name and/or description may receive more weight than data type and/or data size, which in turn may receive more weight than classification label(s).

As another example, the inventors have recognized and appreciated that, to facilitate data conversion, it may be beneficial to identify connections between data tables. For instance, a first table may be connected to a second table if a primary key of the first table is a foreign key of the second table, or vice versa. Additionally, or alternatively, a first table may be connected to a second table if a data field in the first table matches a data field in the second table, where matching between data fields may be determined based on conversion scores.

In some embodiments, connections between data tables may be used to identify a path between a given pair of tables. For instance, a graph may be provided, where each node may represent a data table, and each edge may represent a connection between two tables. Accordingly, one or more suitable optimization techniques (e.g., exact, approximate, and/or heuristic techniques) may be used to identify a shortest path between a first table and a second table. Such a path may then be used to access the second table from the first table.

The inventors have recognized and appreciated that some types of connections may be more desirable than others. For instance, if a data field in a first table is a primary key in a second table, then every record in the first table may correspond to a unique record in the second table, but a record in the second table may correspond to multiple records in the first table. Thus, a connection from the first table to the second table may be stronger than a connection from the second table to the first table.

Accordingly, in some embodiments, if a first table and a second table are connected, there may be two directed edges between these tables. A first edge may be from the first table to the second table, and a second edge may be from the second table to the first table. The two edges may have different costs associated therewith. For instance, an edge representing a stronger connection may be associated with a lower cost. Thus, one or more suitable optimization techniques (e.g., exact, approximate, and/or heuristic techniques) may be used to identify a least costly path between two tables.

It should be appreciated that the techniques introduced above and/or described in greater detail below may be implemented in any of numerous ways, as these techniques are not limited to any particular manner of implementation. Examples of implementation details are provided herein solely for purposes of illustration. Furthermore, the techniques described herein may be used individually or in any suitable combination, as aspects of the present disclosure are not limited to any particular technique or combination of techniques.

FIG. 1 shows an illustrative data conversion engine 100, in accordance with some embodiments. For instance, the data conversion engine 100 may be used to facilitate migration from a source system 105 to a target system 110. This migration may be performed by an organization for any suitable reason. As an example, the migration may be part of a transition from an on-premises computing infrastructure to a cloud computing infrastructure. The source system 105 and the target system 110 may simply be different implementations of the same information management system.

Additionally, or alternatively, the source system 105 and the target system 110 may be different information management systems (e.g., provided by different software vendors). For instance, the source system 105 may be a legacy system that no longer meets the organization's needs, while the target system 110 may provide additional and/or improved functionalities to better support the organization's operations.

In some embodiments, the data conversion engine 100 may be configured to analyze source information 115 to build one or more semantic models for what is stored in the source system 105. The source information 115 may include any suitable information about the source system 105. For instance, the source information 115 may include schemas for data tables in the source system 105.

A schema for a data table may include, without limitation, one or more of the following.

Table name

Names of one or more fields within the table

Natural language descriptions of the one or more fields

Data types of the one or more fields

In some instances, a field may have a data type comprising a code list, which may be a list of allowable values. For instance, a code list for healthcare provider types may have values such as PCP, NP, PA, etc. Each value may have an associated natural language description, such as "Primary Care Physician" for PCP, "Nurse Practitioner" for NP, "Physician Assistant" for PA, etc.

Additionally, or alternatively, a schema may indicate one or more restrictions on a data type of a field. For example, a field may have a data type of character string, but one or more selected characters may be disallowed.

Data sizes of the one or more fields

For instance, a schema may indicate whether a field may be empty.

Additionally, or alternatively, a schema may indicate a minimum length and/or a maximum length of a field having a data type of character string.

Additionally, or alternatively, a schema may indicate a minimum value and/or a maximum value of a field having a data type of integer.

One or more fields that are (collectively) designated as a primary key of the table One or more fields connecting the table to other tables, such as a foreign key pointing to another table.

In some embodiments, the data conversion engine 100 may be configured to crawl the source system 105 to generate a data profile. This may be done in addition to, or instead of, analyzing the source information 115. For instance, the data conversion engine 100 may detect a data field's name, one or more values stored in the data field, and/or one or more patterns in the one or more values. This information may be used to match the data field to an entry in a data dictionary maintained by the data conversion engine 100.

As an example, the data conversion engine 100 may detect that the data field's name is "HCP_Type" and may apply one or more natural language processing (NLP) techniques to match the name "HCP_Type" to an entry in the data dictionary for a term "Healthcare Provider Type."

As another example, a schema may indicate that the data field has a maximum size of 30 characters, but the data conversion engine 100 may detect that no character string stored in the data field is more than 25 characters long. Accordingly, the data conversion engine 100 may match the data field to a data dictionary entry having a maximum data size of 25 characters.

As another example, a schema may indicate that the data field has a data type comprising a first code list of 8 values, but the data conversion engine 100 may detect that only 3 values are stored in the data field (e.g., PCP, NP, and PA), and that one of those 3 values (e.g., PCP) accounts for over a threshold percentage (e.g., 90%) of occurrences.

Accordingly, the data conversion engine 100 may match the data field to a data dictionary entry having a data type comprising a second code list that includes values corresponding to the 3 values that actually occur in the data field. For instance, the values PCP, NP, and PA in the first code list may be mapped to P, N, and A in the second code list, respectively. Some, or none, of the other 5 values in the first code list may have corresponding value(s) in the second code list. The second code list may, although need not, include one or more values that do not correspond to any value in the first code list.

Additionally, or alternatively, the data conversion engine 100 may provide a report to a user showing the 3 detected values (e.g., PCP, NP, and PA) and respective frequencies. The most frequent value (e.g., PCP) may be flagged, and the user may be prompted to confirm that the most frequent value (e.g., PCP) has been correctly mapped to a value in the second code list (e.g., P).

The inventors have recognized and appreciated that such a report may be used to facilitate system migration planning. For instance, if more than 90% of records have a healthcare provider type of "Primary Care Physician," then integration and/or testing efforts may be focused on primary care physicians, instead of nurse practitioners or physician assistants.

In some embodiments, the dictionary entry for the term "Healthcare Provider Type" may store a representative natural language description for the term "Healthcare Provider Type." If a natural language description is provided in a schema for the field "HCP_Type," the data conversion engine 100 may check that the schema description matches the representative description in the dictionary entry. Any one or more suitable matching techniques may be used, such as fuzzy and/or semantic matching techniques.

Additionally, or alternatively, the dictionary entry for the term "Healthcare Provider Type" may store a representative data type, such as a representative code list. The representative code list may include one or more allowable values (e.g., PCP, NP, PA, etc.) and/or associated descriptions (e.g., "Primary Care Physician," "Nurse Practitioner," "Physician Assistant," etc.). The data conversion engine 100 may check that the one or more values stored in the field "HCP_Type" match the representative code list in the dictionary entry.

Referring again to the example of FIG. 1, the data conversion engine 100 may be configured to analyze target information 120 to build one or more semantic models for what is to be stored in the target system 110. The target information 120 may include any suitable information about the target system 110. For instance, the target information 120 may include schemas for data tables in the target system 110. Examples of what may be included in a schema are described above in connection with the source information 115.

Additionally, or alternatively, the target information 120 may include one or more input specifications, which may indicate content and/or format of one or more data load files, one or more load constraints, etc. Examples of load constraints include, but are not limited to, an order in which the one or more files are to be loaded into the target system 110, one or more data type constraints (e.g., one or more disallowed characters), one or more data size constraints (e.g., maximum length of character strings), etc.

In some embodiments, the data conversion engine 100 may use the source information 115, the data profile generated for the source system 105, and/or the target information 120 to match one or more data fields in the target system 110 to one or more data fields in the source system 105.

For instance, the target system 110 may have a patient address field in each patient record, whereas the source system 105 may have a street number field, a street name field, a city name field, etc., in each patient record. Thus, to populate a patient address field in the target system 110, the data conversion engine 100 may retrieve and combine data from multiple fields in the source system 105.

Additionally, or alternatively, the data conversion engine 100 may retrieve data from a field in the source system 105, and use the retrieved data to populate multiple fields in the target system 110. For instance, the source system 105 may have a patient contact field in each patient record, where the patient contact field may store a structured data object, such as a list of contact records. Each contact record may have two fields: contact type (e.g., address, home phone, email, etc.) and contact detail (e.g., 110 ABC Ave., XYZ Town, ZC 01234, 123-456-7890, alice@email_domain.com, etc.). Thus, the data conversion engine 100 may use such a data object to populate multiple fields in a patient record in the target system 110, such as patient address, patient phone, patient email, etc.

In some embodiments, the data conversion engine 100 may generate software code (e.g., a database script) for retrieving data from one or more data fields in the source system 105, and/or transforming the retrieved data. Such software code may be used to prepare data to be loaded into a data field in the target system 110.

For instance, a data field in the target system 110 may store a date in a 6-digit format (e.g., DDMMYY), whereas a matching data field in the source system 105 may store a date in an 8-digit format (e.g., DDMMYYYY). Accordingly, the data conversion engine 100 may convert an 8-digit date from the matching data field into a character string, remove the 5$^{th}$ and 6$^{th}$ character, and convert a resulting character string into a 6-digit date.

Additionally, or alternatively, the data conversion engine 100 may be configured to test the target system 110 after some data has been loaded. For instance, a selected downstream system may be used to generate the same type of report twice, once by accessing data from the source system 105, and separately by accessing data from the target system 110. The data conversion engine 100 may be configured to compare the two output reports. If one or more differences are identified, the data conversion engine 100 may attempt to reconcile such differences.

For example, the data conversion engine 100 may modify the matching of data fields in the target system 110 to data fields in the source system 105, re-load data into the target system 110 according to the modified matching, and generate another report from the target system 110. This may be repeated until a new report matches the report generated from the source system 105.

While certain implementation details are described above in connection with FIG. 1, it should be appreciated that such details are provided solely for purposes of illustration. For example, aspects of the present disclosure are not limited to performing a system migration. In some embodiments, one or more of the techniques described herein may be used to profile and/or cleanse data on an on-going basis.

For instance, the data conversion engine 100 may monitor an information management system, and may examine values stored in data fields (e.g., as described above) to detect potential anomalies. As an example, a potential anomaly may be flagged if, in a certain data field, a value is encountered that does not match any member of a representative code list in a dictionary entry corresponding to the data field.

Moreover, it should be appreciated that aspects of the present disclosure are not limited to how data is accessed from the source system 105, or loaded into the target system 110. In some embodiments, the data conversion engine 100 may interact with the source system 105 and/or the target system 110 via one or more application programming interfaces (APIs), such as one or more database APIs. Additionally, or alternatively, the data conversion engine 100 may be configured to ingest data files from the source system 105, and/or load data files into the target system 110. Any one or more suitable file types may be used, such as flat files (e.g., CSV, XML, etc.).

FIG. 2 shows an illustrative data dictionary 200, in accordance with some embodiments. For instance, the data dictionary 200 may be maintained by the illustrative data conversion engine 100 in the example of FIG. 1, and may be used to generate a data profile for the illustrative source system 105.

In the example of FIG. 2, each entry in the data dictionary 200 may be associated with a term, and may provide a natural language description, a data type, a data size, and/or other information for the term. A term may include a string of one or more characters, such as a token that may result from tokenizing text. For example, a term may include a subword (e.g., "Inv"), a word (e.g., "Inventory"), or a phrase (e.g., "Inventory List").

The inventors have recognized and appreciated that a term may have different meanings when used in different contexts. Accordingly, in some embodiments, an entry in the data dictionary 200 may indicate a context in which the entry is applicable. For instance, an entry for a term "Inventory" may indicate the entry is applicable in all contexts (ALL), while an entry for a term "Inv" may indicate the entry is applicable in an inventory management context (IM).

Although not shown in the example of FIG. 2, the term "Inv" may have another entry that is applicable in a patent law context, where "Inv" may be an abbreviation for the word "Inventor," as opposed to "Inventory."

In some embodiments, an entry in the data dictionary 200 may indicate that a term is related to one or more other terms. For example, the entry for the term "Inv" may indicate that "Inv" is an abbreviation of "Inventory" and "Inventories." Similarly, the entry for the term "Inventory" may indicate that "Inventory" is a singular form of "Inventories," and an expansion of "Inv."

It should be appreciated that the data dictionary 200 may connect a term to any suitable number of one or more related terms, or no related term at all. Moreover, aspects of the present disclosure are not limited to any particular relationship type. Any one or more of the following relationship types, and/or one or more other relationship types, may be used.

| Relationship | Explanation |
|---|---|
| Abbreviation | Shortened form of a word or a phrase |
| Acronym | Abbreviation that is formed from initial letters of several words in a phrase, and is sometimes pronounced as a word |
| Antonym | Word or phrase having an opposite meaning |
| Component | Part of a larger whole (e.g., a word in a phrase) |

| Relationship | Explanation |
| --- | --- |
| Conjugation | Derived form of a verb by inflection (e.g., to indicate voice, tense, number, etc.) |
| Declension | Derived form of a word that is not a verb, by inflection (e.g., to indicate person, gender, number, etc.) |
| Expansion | Converse of abbreviation |
| Generalization | Word or phrase representing a more general concept |
| Inclusion | Converse of component (e.g., a phrase that includes a word) |
| Pluralization | Declension to indicate more than one in number |
| Prefix | Token placed before a word stem |
| Singularization | Declension to indicate one or fewer in number |
| Specialization | Converse of generalization |
| Synonym | Word having the same, or a similar, meaning |
| Alias | Word or phrase which, in a given context, is mapped to another word or phrase (e.g., a more relevant word or phrase for a particular organization or deployment) |

Figure 3:
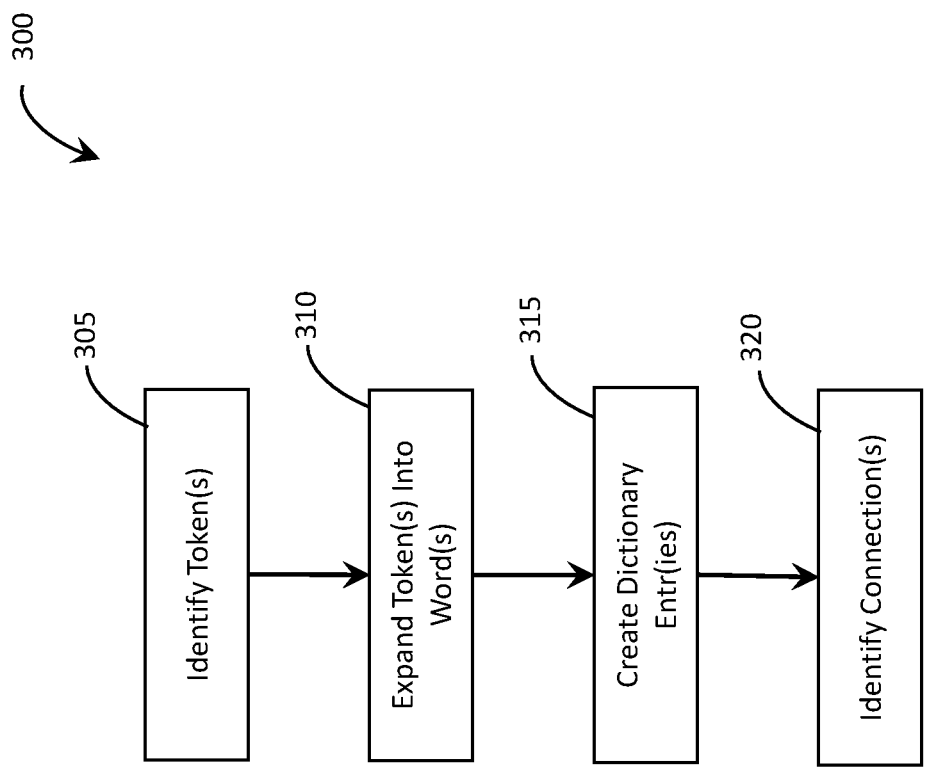
FIG. 3 shows an illustrative process 300 for creating one or more data dictionary entries, in accordance with some embodiments.

FIG. 3 shows an illustrative process 300 for creating one or more data dictionary entries, in accordance with some embodiments. For instance, the process 300 may be used by the illustrative data conversion engine 100 in the example of FIG. 1 to create one or more entries in the illustrative data dictionary 200 in the example of FIG. 2.

In the example of FIG. 3, the data conversion engine 100 extracts information from an existing glossary, and uses the extracted information to create one or more data entries in the data dictionary 200. The glossary may be obtained from any suitable source, such as a data vendor, a vendor of information management software, a trade association, etc. A portion of an illustrative glossary is provided below.

| Abbreviated Term | Unabbreviated Term | Description |
| --- | --- | --- |
| Int_Exp | Interest Expense | . . . |
| Int_Income | Interest Income | . . . |

At act 305, the data conversion engine 100 may tokenize an abbreviated term in the glossary. For instance, two tokens, "Int" and "Exp," may be obtained from "Int Exp." Likewise, two tokens, "Int" and "Income," may be obtained from "Int_Income."

At act 310, the data conversion engine 100 may use corresponding unabbreviated terms in the glossary to expand one or more of the tokens identified at act 305. For instance, the data conversion engine 100 may determine that "Int" is an abbreviation for "Interest," and "Exp" is an abbreviation for "Expense."

At act 315, the data conversion engine 100 may create one or more dictionary entries. For instance, in some embodiments, the data conversion engine 100 may create entries for the terms "Interest Expense" and "Interest Income," with corresponding descriptions from the glossary. If available from the glossary, corresponding data types, data sizes, and/or other information may also be included. Each of these entries may be associated with a context indicating the source of the glossary (e.g., a particular data vendor, software vendor, trade association, etc.).

In some embodiments, the data conversion engine 100 may check if the terms "Interest," "Expense," and "Income" are already in the data dictionary 200. For instance, the data conversion engine 100 may determine that "Expense" and "Income" are already in the data dictionary 200, but "Interest" is not. Accordingly, the data conversion engine 100 may create an entry for the term "Interest."

As an example, the data conversion engine 100 may check if the term "Interest" appears individually in the glossary. If so, a description of "Interest" from the glossary may be used, and the entry may be associated with the context indicating the source of the glossary. If not, the data conversion engine 100 may consult another source of information, and the entry may be associated with a context indicating the other source.

Additionally, or alternatively, if multiple descriptions of "Interest" are available, multiple entries may be created with the same term (i.e., "Interest") but different descriptions and possibly different contexts.

In some embodiments, the data conversion engine 100 may indicate in the entry for "Interest" that "Interest" is a component of "Interest Expense." Additionally, or alternatively, the data conversion engine 100 may indicate in the entry for the term "Interest Expense" that "Interest Expense" includes "Interest." Similarly, the data conversion engine 100 may indicate component and inclusion relationships between "Expense" and "Interest Expense," between "Interest" and "Interest Income," and between "Income" and "Interest Income."

In some embodiments, the data conversion engine 100 may create one or more related entries for the term "Interest." For instance, the data conversion engine 100 may create an entry for "Interests," and may indicate pluralization and singularization relationships between "Interest" and "Interests." Additionally, or alternatively, the data conversion engine 100 may create an entry for "Interested," and may indicate conjugation relationships between "Interest" and "Interested."

In some embodiments, the data conversion engine 100 may check if the terms "Int" and "Exp" are already in the data dictionary 200. For instance, the data conversion engine 100 may determine that "Exp" is already in the data dictionary 200, but "Int" is not. Accordingly, the data conversion engine 100 may create an entry for the term "Int." The entry may indicate that "Int" is an abbreviation for "Interest," and may be associated with the context indicating the source of the glossary. Additionally, or alternatively, the data conversion engine 100 may indicate in the entry for the term "Interest" that "Interest" is an expansion of "Int" in the context indicating the source of the glossary.

In some embodiments, the data conversion engine 100 may check an existing entry for the term "Exp" to determine if the entry matches the term "Expense." For instance, the existing entry for the term "Exp" may indicate that "Exp" is an abbreviation for "Expiration." Thus, the data conversion engine 100 may determine that the existing entry does not match the term "Expense."

Accordingly, the data conversion engine 100 may create a new entry for the term "Exp." This new entry may indicate that "Exp" is an abbreviation for "Expense," and may be associated with the context based on the source of the glossary. Additionally, or alternatively, the data conversion engine 100 may indicate in the entry for the term "Expense" that "Expense" is an expansion of "Exp" in the context indicating the source of the glossary.

Referring again to the example of FIG. 3, the data conversion engine 100 may, at act 320, identify one or more additional connections between dictionary entries. For instance, the data conversion engine 100 may search the data dictionary 200 for one or more terms in which the term "Interest" occurs, other than "Interest Expense" and "Interest Income." For instance, the data conversion engine 100 may find an entry for "Interest Rate." Accordingly, the data conversion engine 100 may modify the entry for "Interest Rate" and the entry for "Interest" to indicate inclusion and component relationships, respectively.

Although certain implementation details are described above in connection with FIGS. 2-3, it should be appreciated that such details are provided solely for purposes of illustration. For example, aspects of the present disclosure are not limited to indicating any particular type of relationship between dictionary entries, or any relationship at all.

In some embodiments, the data conversion engine 100 may obtain information from one or more sources other than the glossary, such as information indicating synonym and/or antonym relationships. For instance, the information may indicate that "Rack Rate" and "Discount" are antonyms, and likewise "Rack Rate" and "Sale" are antonyms. Thus, the data conversion engine 100 may infer that "Sale" and "Discount" are likely synonyms. The data conversion engine 100 may then use such information to create new entries and/or indicate relationships between entries.

Figure 4A:
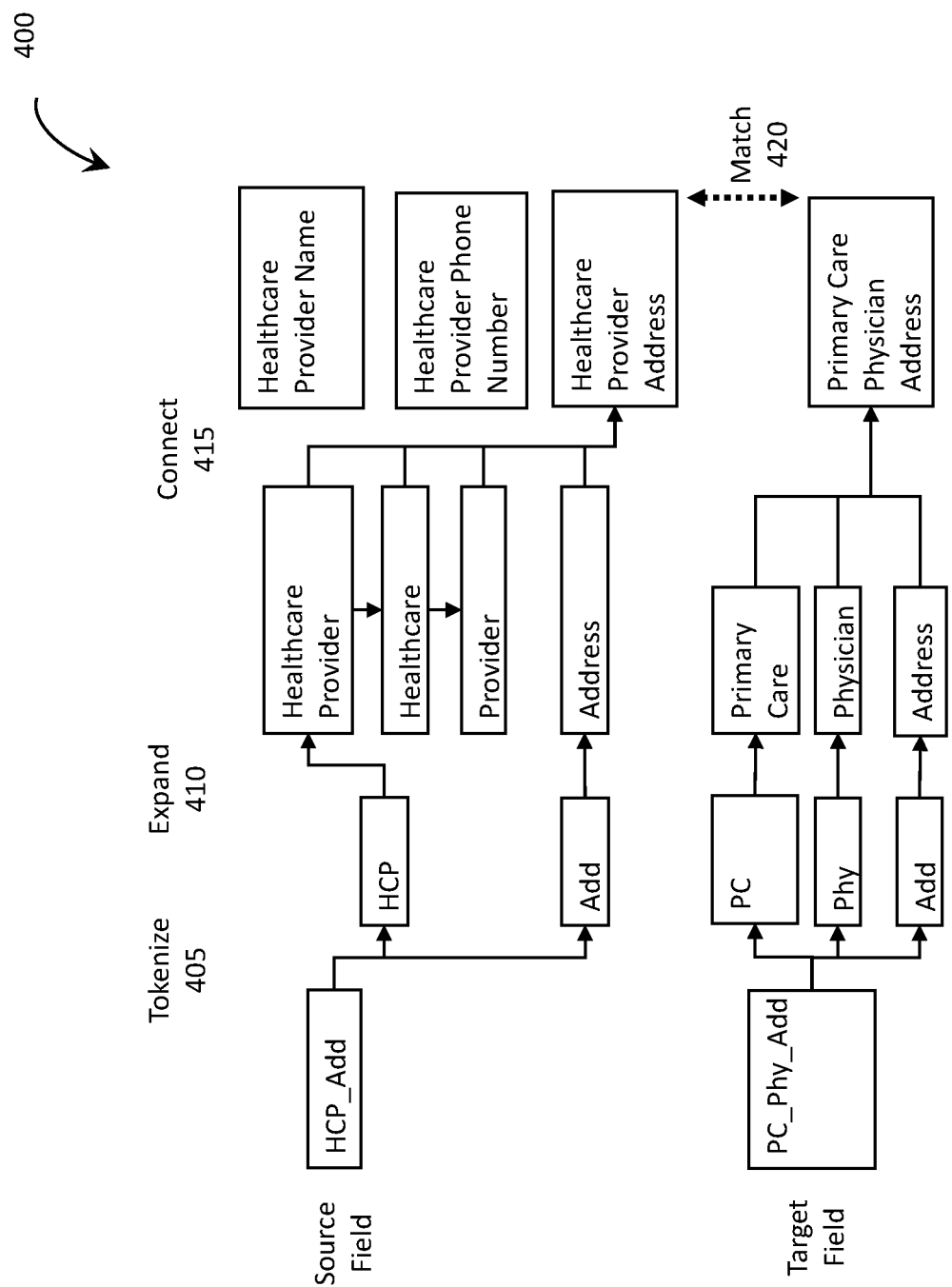
FIG. 4A shows an illustrative process 400 for processing a name of a data table or data field, in accordance with some embodiments.

FIG. 4A shows an illustrative process 400 for processing a name of a data table or data field, in accordance with some embodiments. For instance, the process 300 may be used by the illustrative data conversion engine 100 in the example of FIG. 1 to match a data field in the illustrative target system 110 to a data field in the illustrative source system 105.

In the example of FIG. 3, the source system 105 has data fields named, respectively, "HCP_Name," "HCP_Phone," and "HCP_Add," whereas the target system 110 has a data field named "PC_Phy_Add." At act 405, the data conversion engine 100 may tokenize "HCP_Add" into "HCP" and "Add," and "PC_Phy_Add" into "PC," "Phy," and "Add."

At act 410, the data conversion engine 100 may expand the terms "HCP" and "Add" into "Healthcare Provider" and "Address," and the terms "PC," "Phy," and "Add" into "Primary Care," "Physician," and "Address," respectively. This may be done in any suitable manner. For instance, the data conversion engine 100 may attempt to match the terms "HCP" and "Add" to entries in the illustrative data dictionary 200 in the example of FIG. 2, and likewise for the terms "PC," "Phy," and "Add."

The inventors have recognized and appreciated that, in some instances, a term may have different meanings when used in different contexts. Accordingly, in some embodiments, the data conversion engine 100 may match a term to an entry in the data dictionary 200 in a manner that is context dependent.

Figure 4B:
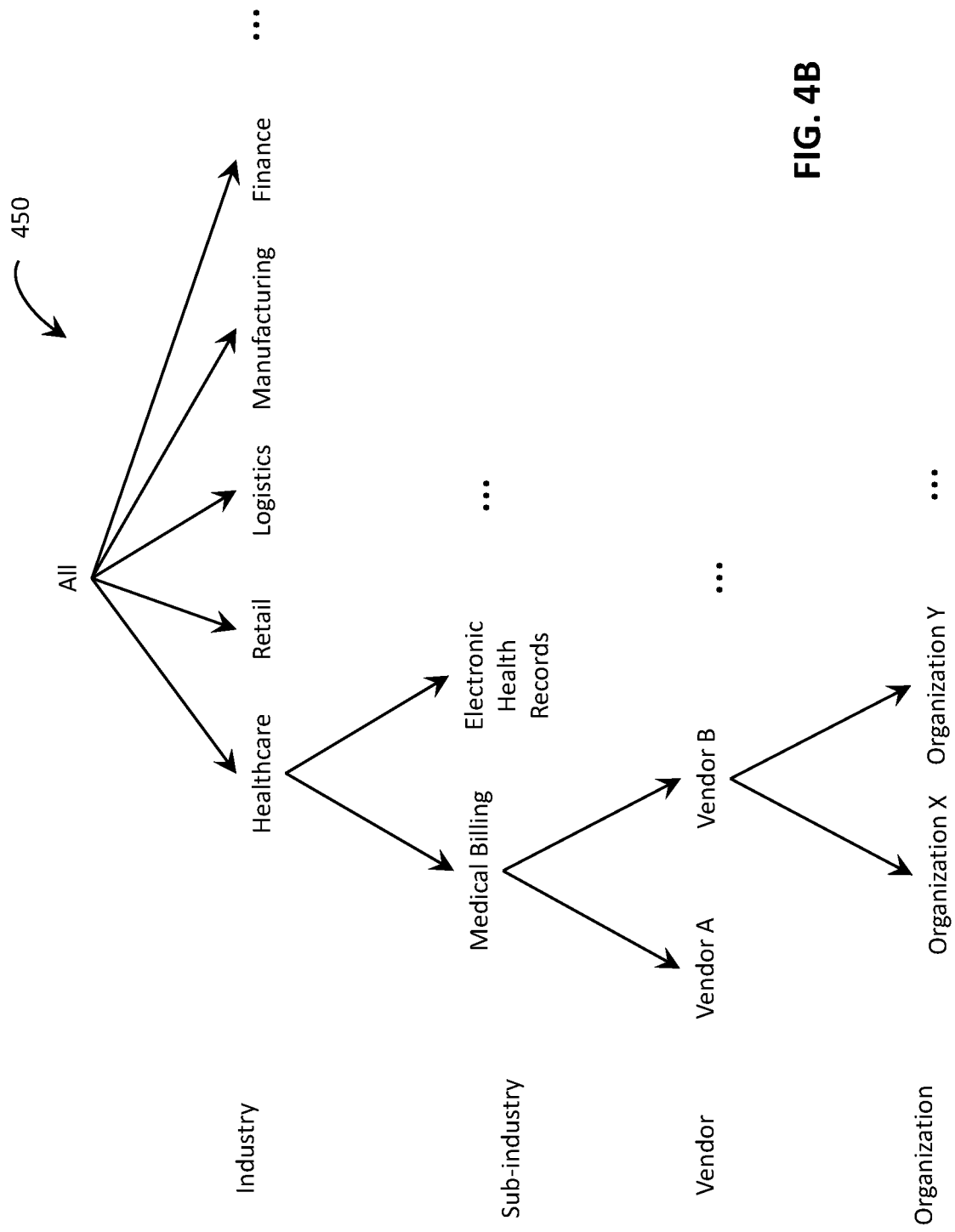
FIG. 4B shows an illustrative context hierarchy 450, in accordance with some embodiments.

FIG. 4B shows an illustrative context hierarchy 450, in accordance with some embodiments. In this example, the context hierarchy 450 has four levels.

At a top level, there may be a universal context (e.g., ALL).
For instance, terms and corresponding descriptions from a general-purpose dictionary (e.g., Merriam-Webster) may be associated with the universal context.

Below the universal context, there may be contexts associated with different industries, such as healthcare, retail, logistics, manufacturing, finance, etc.
For instance, terms and corresponding descriptions from a glossary published by a trade association for an industry may be associated with the context for that industry.

Below each industry context, there may be contexts associated with different sub-industries. As an example, below healthcare, there may be medical billing, electronic health records, etc.
For instance, terms and corresponding descriptions from a glossary published by a trade association for a sub-industry may be associated with the context for that sub-industry.

Below each sub-industry context, there may be contexts associated with different software vendors, data vendors, etc.
For instance, terms and corresponding descriptions from a glossary provided by a vendor may be associated with the context for that vendor.

Below each vendor context, there may be contexts associated with different organizations.
For instance, a software vendor may provide a multi-purpose and/or multi-tenant application. Such an application may be customized differently for different organizations. As an example, an organization may add one or more custom data tables and/or one or more custom data fields in a default data table.

Although not shown in FIG. 4B, below each organization context, there may be contexts associated with different deployments.
For instance, an organization may have multiple facilities (e.g., different hospitals, clinics, etc. in a healthcare network). A software application may be customized differently for the different facilities. As an example, a facility (e.g., a specialist clinic) may add one or more custom data tables and/or one or more custom data fields in a default data table.

It should be appreciated that the context hierarchy 450 is merely illustrative. Aspects of the present disclosure are not limited to a context hierarchy having any number of one or more levels, or any number of one or more contexts, or to any context hierarchy at all.

Returning to the example of FIG. 4A, the data conversion engine 100 may, at act 410, use the context hierarchy 450 to match a term to an entry in the data dictionary 200. For instance, for the term "HCP," the data conversion engine 100 may first search for a match among entries associated with a context for the source system 105. If no match is found in that context, the data conversion engine 100 may move up one level in the context hierarchy 450, and may search for a match among entries associated with the medical billing context.

If no match is found in the medical billing context, the data conversion engine 100 may move up another level in the context hierarchy 450, and may search for a match among entries associated with the healthcare context.

If no match is found in the healthcare context, the data conversion engine 100 may move up yet another level in the context hierarchy 450, and may search for a match among entries associated with the universal context.

The inventors have recognized and appreciated that an entry at a higher level in the context hierarchy 450 may have more related entries. For instance, "Inv" in the universal context may be an abbreviation of "Inventory" and an abbreviation of "Inventor." By contrast, "Inv" in the retail context may only be an abbreviation of "Inventory." Therefore, a match at a lower level in the context hierarchy 450 may narrow a pool of candidate terms, which may improve accuracy and/or efficiency.

In some embodiments, the data conversion engine 100 may check if the terms "HCP," "Add" (in the context for the source system 105), "PC," "Phy," and "Add" (in a context for the target system 110) are already in the data dictionary 200, and may add one or more entries, as appropriate. This may be done in any suitable manner, for example, as described in connection with act 315 in the illustrative process 300 in the example of FIG. 3.

Continuing to act 415, the data conversion engine 100 may use the data dictionary 200 to identify one or more related terms. For instance, the data conversion engine 100 may determine that "Healthcare Provider" includes "Healthcare" and "Provider," and that both "Healthcare Provider" and "Address" are components of "Healthcare Provider Address." Accordingly, the data conversion engine 100 may match the data field "HCP_Add" in the source system 105 to "Healthcare Provider Address."

Similarly, the data conversion engine 100 may determine that "Primary Care," "Physician," and "Address" are components of "Primary Care Physician Address." Accordingly, the data conversion engine 100 may match the data field "PC_Phy_Add" in the target system 110 to "Primary Care Physician Address."

Although not shown in detail in FIG. 4A, the data conversion engine 100 may match the data fields "HCP_Name" and "HCP_Phone," in the source system 105 to "Healthcare Provider Name" and "Healthcare Provider Phone Number," respectively.

Continuing to act 420, the data conversion engine 100 may attempt to match the data field "PC_Phy_Add" in the target system 110 to a data field in the source system 105, such as one of the data fields "HCP_Name," "HCP_Phone," and "HCP_Add."

FIG. 4C shows an illustrative process 460 for matching a target data structure to a source data structure, in accordance with some embodiments. A target data structure may include one or more data tables and/or one or more data fields in a target system, such as the illustrative target system 110 in the example of FIG. 1. Likewise, a source data structure may include one or more data tables and/or one or more data fields in a source system, such as the illustrative source system 105 in the example of FIG. 1.

In some embodiments, given a target data structure, a conversion score may, at act 465, be computed for each of a plurality of source data structures. Then, at act 470, the target data structure may be matched to one of the plurality of source data structures based on the respective conversion scores.

For instance, given a data field in the target system 110 (a target field, for short), the illustrative data conversion engine 100 in the example of FIG. 1 may compute respective conversion scores between that target field and multiple data fields in the source system 105 (source fields, for short). The target field may then be matched to a source field having a highest conversion score for that target field.

In some embodiments, the process 460 may be used at act 420 in the example of FIG. 4A to match the illustrative data field "PC_Phy_Add" to one of the illustrative data fields "HCP_Name," "HCP_Phone," and "HCP_Add." For instance, the data conversion engine 100 may compute a conversion score between the target field "PC_Phy_Add" and the source field "HCP_Name," a conversion score between the target field "PC_Phy_Add" and the source field "HCP_Phone," and a conversion score between the target field "PC_Phy_Add" and the source field "HCP_Add." A source field having a highest conversion score, such as "HCP_Add," may be selected as a match for the target field "PC_Phy_Add."

Conversion scores may be computed in any suitable manner. In some embodiments, the data conversion engine 100 may, for each data field, determine a feature vector, which may include one or more values associated with the data field, such as name, description, data type, data size, one or more classification labels, one or more relationships with other data fields, etc. A conversion score between two data fields may be computed based on the respective feature vectors. For instance, a sub-score may be determined for each dimension, and one or more sub-scores may be combined to determine an overall score.

In some embodiments, features may be weighted for purposes of computing a conversion score. For instance, name and/or description may receive more weight than data type and/or data size, which in turn may receive more weight than classification(s).

A sub-score may be determined in any suitable manner. For instance, one or more NLP techniques (e.g., syntactic similarity, semantic similarity, etc.) may be used to determine a sub-score for the name dimension, and/or a sub-score for the description dimension. As an example, although "Healthcare Provider" and "Primary Care Physician" may have low syntactic similarity (e.g., based on a bag-of-words measure), the terms may be semantically related (e.g., "Healthcare Provider" being a generalization of "Primary Care Physician" in the data dictionary 200). Therefore, the target field "PC_Phy_Add" and the source field "HCP_Add" may have a relatively high sub-score in the name dimension (although the sub-score would have been higher if the fields were to match both syntactically and semantically).

In some embodiments, a sub-score may be negative. For instance, if two data fields have matching types, but drastically different sizes, then the data type dimension may have a positive sub-score of a smaller magnitude, and the data size dimension may have a negative sub-score of a larger magnitude. In this manner, an overall conversion score for the data fields may be low, despite the matching types.

In some embodiments, a sub-score may be determined based on a classification. For instance, both the target field "PC_Phy_Add" and the source field "HCP_Add" may be classified as an address field, whereas the source field "HCP_Phone" may be classified as a phone number field. Accordingly, a sub-score for the target field "PC_Phy_Add" and the source field "HCP_Add" in a classification dimension may be higher than that for the target field "PC_Phy_Add" and the source field "HCP_Phone."

It should be appreciated that aspects of the present disclosure are not limited to having any number of one or more classification dimensions, or any classification dimension at all. Moreover, any one or more suitable classification techniques may be used, such as supervised and/or unsupervised machine learning techniques. For instance, in some embodiments, training data comprising feature vectors of labeled data fields may be used to train one or more classifiers, which may include a neural network classifier, a decision tree classifier, an ensemble learning classifier, etc.

Additionally, or alternatively, one or more clustering techniques may be used to analyze feature vectors of unlabeled data fields, to detect potential patterns. A detected pattern may then be used by a classifier to label data fields.

Any suitable set of features may be used for classification, such as one or more of the features used for computing conversion scores, and/or one or more other features.

Although certain implementation details are described above in connection with FIGS. 4A-C, it should be appreciated that such details are provided solely for purposes of illustration. For instance, in some embodiments, one or more classifications of data fields may be used to eliminate matching candidates, in addition to, or instead of, being used to compute conversion scores. Thus, given a target field, conversion scores may be computed only for those source fields having one or more matching classifications, as opposed to all source fields. This may improve performance of the data conversion engine 100.

Moreover, aspects of the present disclosure are not limited to classifying data fields, or to performing any classification at all. In some embodiments, data tables may be classified in a similar manner as data fields. For instance, one or more features may be determined for a data table, such as name, description, one or more features of data fields in the table (e.g., name, description, data type, data size, one or more data field classifications, one or more relationships with other data fields, etc.), one or more connections to other data tables, etc.

As described above, a conversion score may be computed based on an extent to which a name of a source field (e.g., "HCP_Add") matches a name of a target field (e.g., "PC_Phy_Add"). However, the inventors have recognized and appreciated that, in some instances, a field may have an uninformative name. For instance, a software application may have one or more data tables and/or one or more data fields that are designed to be customized for an organization (e.g., a healthcare network) or a deployment within the organization (e.g., a specialty clinic within the healthcare network). Such a data table or data field may have an uninformative name (e.g., "Custom_Text"), which may be mapped to a display name when the data table or data field is customized.

FIG. 4D shows an illustrative data table 480, in accordance with some embodiments. For instance, the data table 480 may be part of the illustrative source system 105 or the illustrative target system 110 in the example of FIG. 1.

In the example of FIG. 4D, the data table 480 has two customizable data fields, "Custom_Text1" and "Custom_Code1." These data fields may be customized differently by different organizations. For instance, Organization X may map "Custom_Text1" to a display name "Policy Name," whereas Organization Y may map "Custom_Text1" to a display name "Issuer Name." Additionally, or alternatively, Organization X may map "Custom_Code1" to a display name "Policy Type," whereas Organization Y may map "Custom_Code1" to a display name "State of Issuance."

The inventors have recognized and appreciated that field names such as "Custom_Text1" and "Custom_Code1" may not be suitable for use in matching a target field to a source field (e.g., via the illustrative process 400 in the example of FIG. 4A). Accordingly, in some embodiments, a term may be created for a custom data table or data field, and may be mapped to a more informative term (e.g., a display name for the custom data table or data field).

FIG. 4E shows the illustrative data dictionary 200 in the example of FIG. 2, with one or more entries for aliases, in accordance with some embodiments. For instance, a new term may be created for the "Custom_Text1" field in the illustrative data table 480 in the example of FIG. 4D, and one or more entries may be added for the new term.

In this example, the new term is a combination of a name of the data table 480 (i.e., "Policy") and a name of the data field (i.e., "Custom_Text1"). However, it should be appreciated that aspects of the present disclosure are not limited to creating a new term in any particular manner, or at all.

In some embodiments, an entry may have an associated context. For instance, a first entry may be associated with a context for Organization X, whereas a second entry may be associated with a context for Organization Y.

Additionally, or alternatively, an entry may indicate an alias relationship. For instance, the first entry may indicate the new term is an alias for "Policy Name," which may be a display name assigned by Organization X to the "Custom_Text1" field. Likewise, the second entry may indicate the new term is an alias for "Issuer Name," which may be a display name assigned by Organization Y to the "Custom_Text1" field.

Although not shown in FIG. 4E, a new term (e.g., "Policy_Custom_Code1") may be created for the "Custom_Code1" field in the data table 480, and similar entries may be added to map the new term to "Policy Type" in the context for Organization X and "State of Issuance" in the context for Organization Y, respectively.

In this manner, the data conversion engine 100 may use a custom data table name and/or a custom data field name to look up, from the data dictionary 200, a meaningful name for a given context (e.g., at act 415 in the example of FIG. 4A).

Although certain implementation details are described above in connection with FIGS. 4D-E, it should be appreciated that such details are provided solely for purposes of illustration. For example, aspects of the present disclosure are not limited to having different aliases for different organizations. Additionally, or alternatively, there may be different aliases for different deployments within the same organization.

FIG. 5 shows an illustrative process 500 for converting data from a source data structure into data to be loaded into a target data structure, in accordance with some embodiments. For instance, the process 500 may be performed after a target data structure has been matched to a source data structure via the illustrative process 460 in the example of FIG. 4C.

At act 505, data may be accessed from the matched source data structure. Then, at act 510, the accessed data may be used to prepare data to be loaded into the target data structure. For instance, the accessed data may be filtered, cleansed, reformatted, combined, or otherwise transformed.

In some embodiments, the target data structure may include a data table in a target system, such as the illustrative target system 110 in the example of FIG. 1. This data table may have a target field that is designated as a primary key, and one or more other target fields. To populate a record in this data table, a value of the primary key may be used to access data from the matched source data structure, and the accessed data may be used to prepare data to be loaded into the one or more other target fields in the record.

In some embodiments, the matched source data structure may include multiple data fields in a source system, such as the illustrative source system 105 in the example of FIG. 1.

The inventors have recognized and appreciated that, in some instances, the target field designated as a primary key may be matched to a first source field, while another target field may be matched to a second source field that does not reside in the same data table as the first source field. Thus, to reach the second source field from the first source field, the illustrative data conversion engine 100 in the example of FIG. 1 may have to traverse multiple source tables. Accordingly, it may be beneficial to identify connections between data tables, so that the data conversion engine 100 may traverse the data tables efficiently.

Figure 6A:
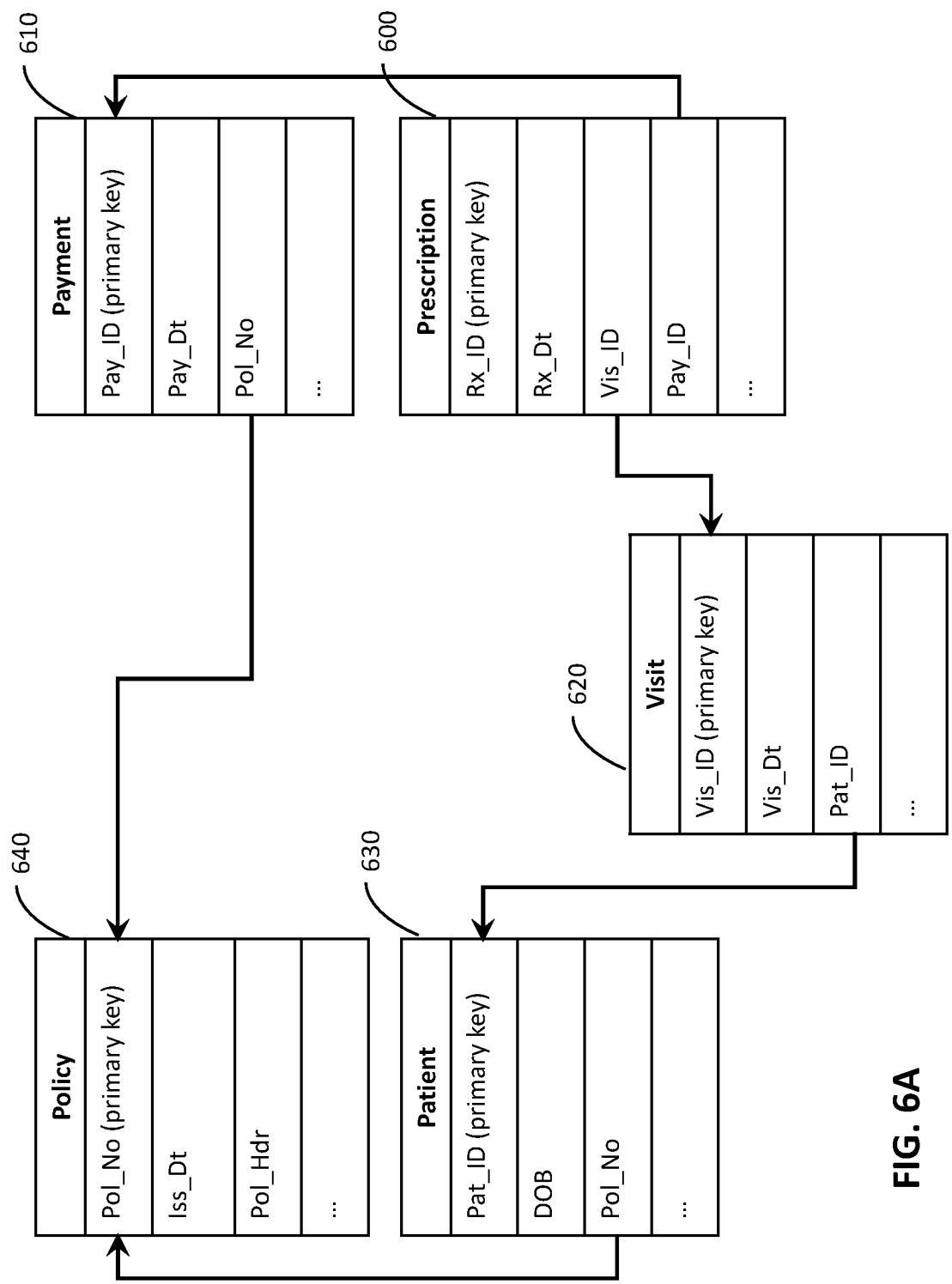
FIG. 6A shows illustrative data tables 600, 610, 620, 630, and 640, in accordance with some embodiments.

FIG. 6A shows illustrative data tables 600, 610, 620, 630, and 640, in accordance with some embodiments. For instance, the data tables 600, 610, 620, 630, and 640 may be part of the illustrative source system 105 in the example of FIG. 1.

In the example of FIG. 6A, the table 600 has a foreign key "Pay_ID" pointing to the table 610, and a foreign key "Vis_ID" pointing to the table 620. In turn, the table 610 has a foreign key "Pol_No" pointing to the table 640, while the table 620 has a foreign key "Pat_ID" pointing to the table 630, and the table 630 has a foreign key "Pol_No" pointing to the table 640. The fields "Pay_ID," "Vis_ID," "Pat_ID," and "Pol_No" are primary keys of the tables 610, 620, 630, and 640, respectively.

FIG. 6B shows an illustrative data table 650, in accordance with some embodiments. For instance, the data table 650 may be part of the illustrative target system 110 in the example of FIG. 1.

In some embodiments, given a record in the table 650 of the target system 110, the illustrative data conversion engine 100 in the example of FIG. 1 may use a prescription identifier stored in an "Rx_ID" field to retrieve a policy holder name to be stored in a "Pol_Hdr" field.

For instance, the data conversion engine 100 may use the illustrative process 400 in the example of FIG. 4A to match the target field "Rx_ID" in the table 650 to the source "Rx_ID" field in the table 600. Likewise, the data conversion engine 100 may use the process 400 to match the target "Pol_Hdr" field in the table 650 to the source "Pol_Hdr" field in the table 640. Accordingly, the data conversion engine 100 may attempt to use the prescription identifier to navigate from the table 600 to the table 640.

The inventors have recognized and appreciated that there are multiple paths to navigate from the table 600 to the table 640. For instance, because the "Rx_ID" field is a primary key of the table 600, the prescription identifier may be used to identify a unique record in the table 600, which may include a visit identifier. Similarly, the visit identifier may be used to identify a patient identifier from the table 620, the patient identifier may be used to identify a policy number from the table 630, and the policy number may be used to identify a policy holder name from the table 640.

Additionally, or alternatively, a payment identifier from the unique record in the table 600 may be used to identify a policy number from the table 610, and the policy number may be used to identify a policy holder name from the table 640.

The inventors have recognized and appreciated that the path through the table 610 may be more desirable than the path through the tables 620 and 630, because the former path may involve fewer hops, and therefore may be more efficient. Accordingly, in some embodiments, one or more suitable optimization techniques (e.g., exact, approximate, and/or heuristic techniques) may be used to identify a shortest path between the table 600 and the table 640.

For instance, a graph may be provided, where each node may represent a data table, and each edge may represent a connection between two tables. A connection of any suitable type may be represented as an edge. As an example, a first table may be connected to a second table if a primary key of the first table is a foreign key of the second table, or vice versa. Additionally, or alternatively, a first table may be connected to a second table if a data field in the first table matches a data field in the second table. Matching between data fields may be determined in any suitable manner, for example, based on conversion scores as described above in connection with the example of FIG. 4A.

In some embodiments, a path (e.g., a shortest path) from one data table to another may be used to generate a query. For instance, with reference to FIGS. 6A-B, a prescription identifier (which is a value of a primary key of the table 650) may be used to look up a record from the table 600, which may include a payment identifier. The payment identifier may, in turn, be used to look up a record from the table 610, which may include a policy number. The policy number, in turn, may be used to look up a record from the table 640, which may include a policy holder name. The policy holder name may be used to populate a record in the table 650.

Figure 7A:
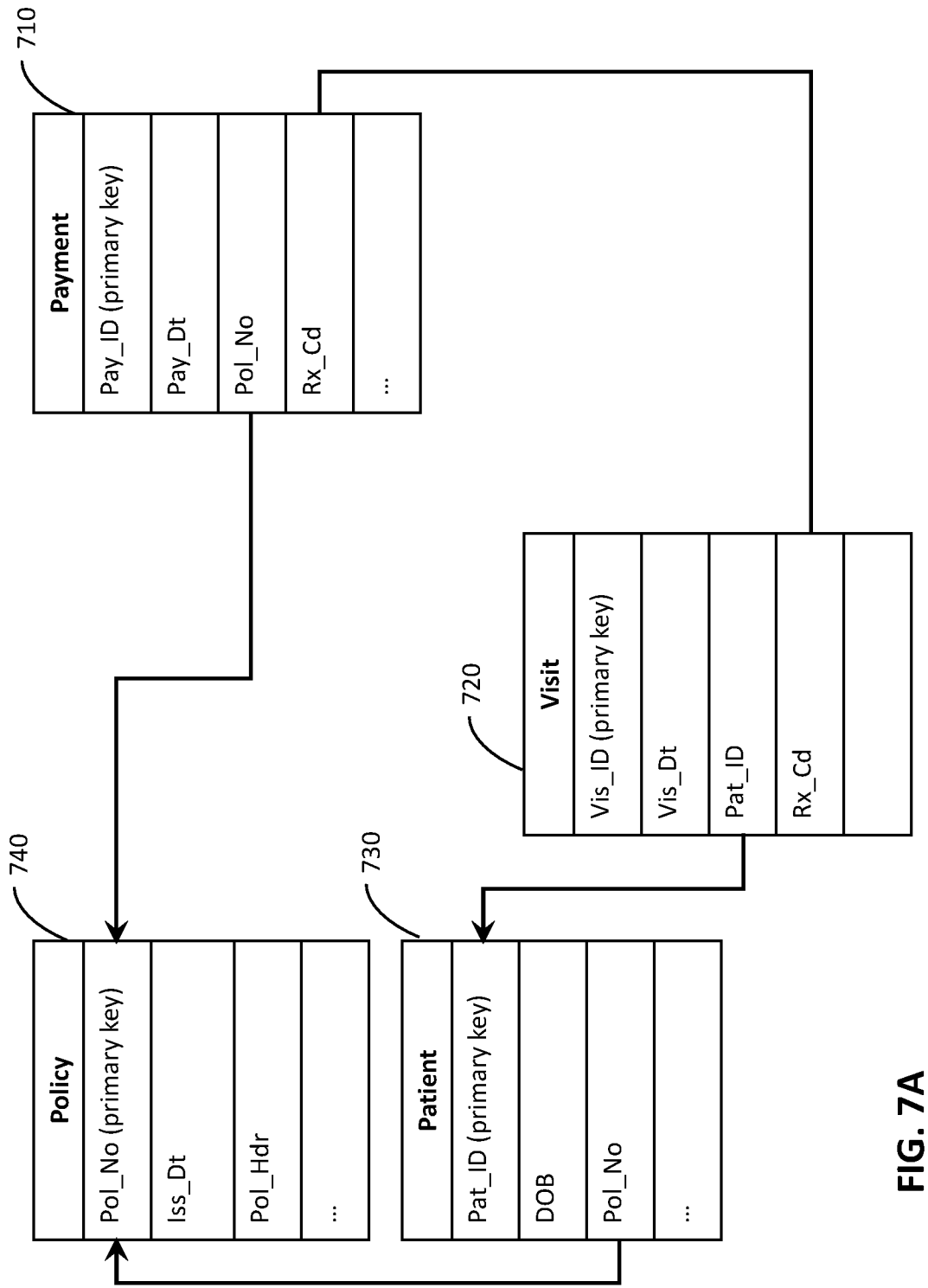
FIG. 7A shows illustrative data tables 710, 720, 730, and 740, in accordance with some embodiments.

FIG. 7A shows illustrative data tables 710, 720, 730, and 740, in accordance with some embodiments. For instance, the data tables 710, 720, 730, and 740 may be part of the illustrative source system 105 in the example of FIG. 1, and may be similar to the illustrative data tables 610, 620, 630, and 640 in the example of FIG. 6A.

In the example of FIG. 7A, there is no prescription table like the illustrative table 600 in the example of FIG. 6A. Instead, the tables 710 and 720 may both have a "Rx_Cd" field, which may store a prescription code. The "Rx_Cd" field may not be a primary key in either table. Thus, given a record in the table 710, there may be zero or more records in the table 720 with the same prescription code, and vice versa.

Nevertheless, the illustrative data conversion engine 100 in the example of FIG. 1 may use the illustrative process 400 in the example of FIG. 4A to match the "Rx_Cd" field in the table 710 to the "Rx_Cd" field in the table 720. A connection may therefore be established between the tables 710 and 720.

FIG. 7B shows an illustrative data table 750, in accordance with some embodiments. For instance, the data table 750 may be part of the illustrative target system 110 in the example of FIG. 1, and may be similar to the illustrative data table 650 in the example of FIG. 6B.

In some embodiments, given a record in the table 750 of the target system 110, the data conversion engine 100 may use a visit identifier stored in an "Vis_ID" field to retrieve a policy holder name to be stored in a "Pol_Hdr" field.

In this example, there are two paths from the table 720 to the table 740, through the table 710 and the table 730, respectively. Each of these paths involves two hops. However, the inventors have recognized and appreciated that the path through the table 730 may be more desirable than the path through the table 710, because the connections along the path through the table 730 are based on primary keys, whereas the connection between the tables 710 and 720 is of a weaker type.

Accordingly, in some embodiments, a graph may be provided, where each node may represent a data table, and each edge may be associated with a cost that is indicative of a strength of a connection between two tables. For instance, an edge representing a stronger connection may be associated with a lower cost. Thus, one or more suitable optimization techniques (e.g., exact, approximate, and/or heuristic techniques) may be used to identify a least costly path between two tables.

Additionally, or alternatively, the edges in the graph may be directed. Accordingly, if a first table and a second table are connected, there may be two directed edges between these tables. A first edge may be from the first table to the second table, and a second edge may be from the second table to the first table.

In some embodiments, the two edges may have different costs associated therewith. For example, if the first edge (from the first table to the second table) represents a primary key in the second table, but the second edge (from the second table to the first table) does not represent a primary key in the first table, then every record in the first table may correspond to a unique record in the second table via the first edge, but a record in the second table may correspond to multiple records in the first table via the second edge. Thus, the first edge may be associated with a lower cost than the second edge.

In some embodiments, a path (e.g., a least costly path) from one data table to another may be used to generate a query. For instance, with reference to FIGS. 7A-B, a visit identifier (which is a value of a primary key of the table 750) may be used to look up a record from the table 720, which may include a patient identifier. The patient identifier may, in turn, be used to look up a record from the table 730, which may include a policy number. The policy number, in turn, may be used to look up a record from the table 740, which may include a policy holder name. The policy holder name may be used to populate a record in the table 750.

In some embodiments, a cost associated with an edge from a first table to a second table may be indicative of a degree of predictiveness. For instance, if the edge represents a primary key in the second table, then every record in the first table may correspond to a unique record in the second table via that edge. Thus, the edge may have a high degree of predictiveness.

If the edge does not represent a primary key in the second table, but nearly every record in the first table corresponds to a unique record in the second table via the edge, then the edge may nonetheless have a relatively high degree of predictiveness. Likewise, if every record in the first table corresponds to at most a few records in the second table via the edge, then the edge may also have a relatively high degree of predictiveness.

The inventors have recognized and appreciated that, in some instances, it may not be possible to find a path with a high degree of predictiveness. For instance, referring again to the example of FIG. 7A, if the table 730 is not present, then the path through the table 710 may be chosen, even though an edge from the table 720 to the table 710 may not have a high degree of predictiveness.

Since the "Vis_ID" field is a primary key of the table 720, the visit identifier may be used to identify a unique record in the table 720, which may include a prescription code. This prescription code may be used to look up the table 710, which may return multiple records. Each such record may include a policy number, which may be used to identify a policy holder name from the table 740.

If the multiple records returned from the table 710 all store the same policy number, then a unique policy holder name may be returned. Likewise, if the multiple records returned from the table 710 store different policy numbers, but somehow the different policy numbers all lead to the same policy holder name, that policy holder name may be returned.

Otherwise, additional information may be used to select a policy number and/or a policy holder name. For instance, if a record returned from the table 710 has a payment date that is before a visit date in the unique record in the table 720, that record from the table 710 may be eliminated. Once all such record(s) are eliminated, a record with a payment that is closest to the visit date may be selected.

Additionally, or alternatively, a message may be displayed to notify a user of a potential ambiguity.

Figure 8A:
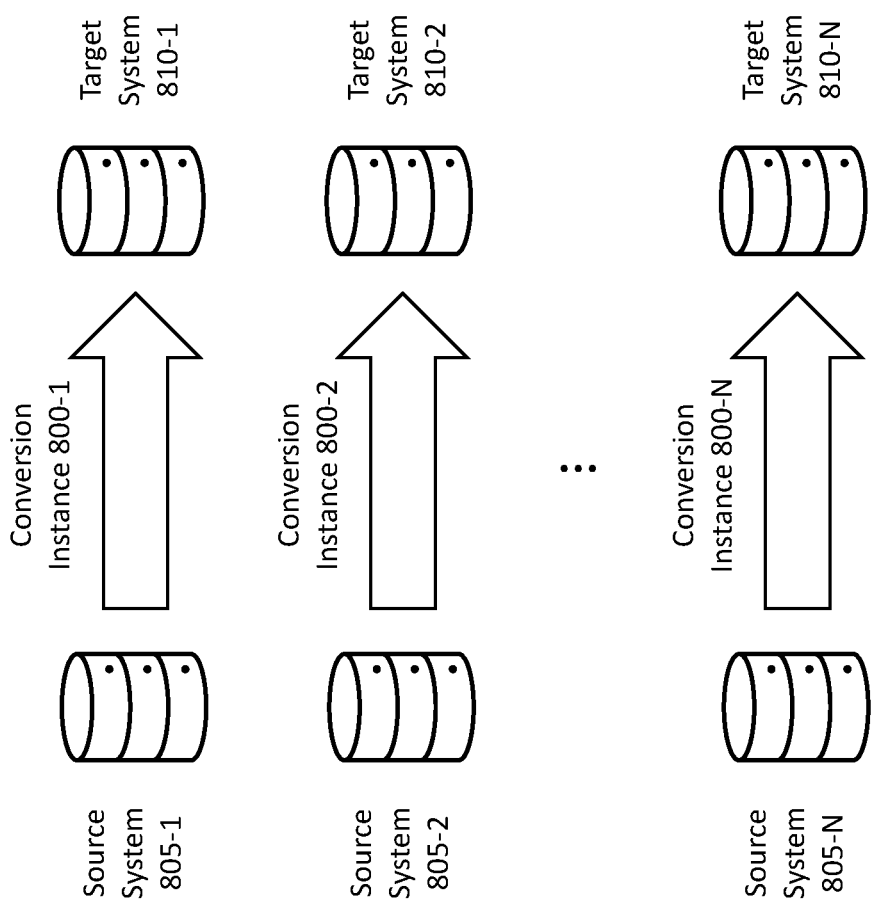
FIG. 8A shows illustrative conversion instances 800-1, 800-2, . . . , 800-N, in accordance with some embodiments.

FIG. 8A shows illustrative conversion instances 800-1, 800-2, . . . , 800-N, in accordance with some embodiments. Each conversion instance 800-$n$ ($n=1$, . . . , N) may be a result of using the illustrative data conversion engine 100 the example of FIG. 1 to perform data conversion for a source system 805-$n$ and a target system 810-$n$.

For example, the conversion instance 800-$n$ may include matchings from data structures in the target system 810-$n$ to respective data structures in the source system 805-$n$ (e.g., as described above in connection with the example of FIG. 4C). Additionally, or alternatively, the conversion instance 800-$n$ may include queries for retrieving data from the source system 805-$n$ and/or transforming the retrieved data in preparation for loading into the target system 810-$n$ (e.g., as described above in connection with the example of FIG. 5).

The inventors have recognized and appreciated that, as the data conversion engine 100 encounters more source systems and target systems over time, certain patterns may emerge. As an example, if the source systems 805-1 and 805-2 are instances of the same software application A, and the target systems 810-1 and 810-2 are instances of the same software application B, then the conversion instances 800-1 and 800-2 may be substantially similar. Such conversion instances may be referred to as having the same type.

As another example, if the conversion instances 800-1, 800-2, . . . , 800-N all have the same type, but the conversion instances 800-1 and 800-2 are in the same industry or sub-industry (e.g., medical billing), while the other conversion instances are not in that industry or sub-industry, then the conversion instances 800-1 and 800-2 may be more similar to each other than to the other conversion instances.

Accordingly, in some embodiments, techniques are provided for leveraging previously performed data conversions to improve efficiency and/or accuracy of future data conversions.

Figures 8B, 8C:
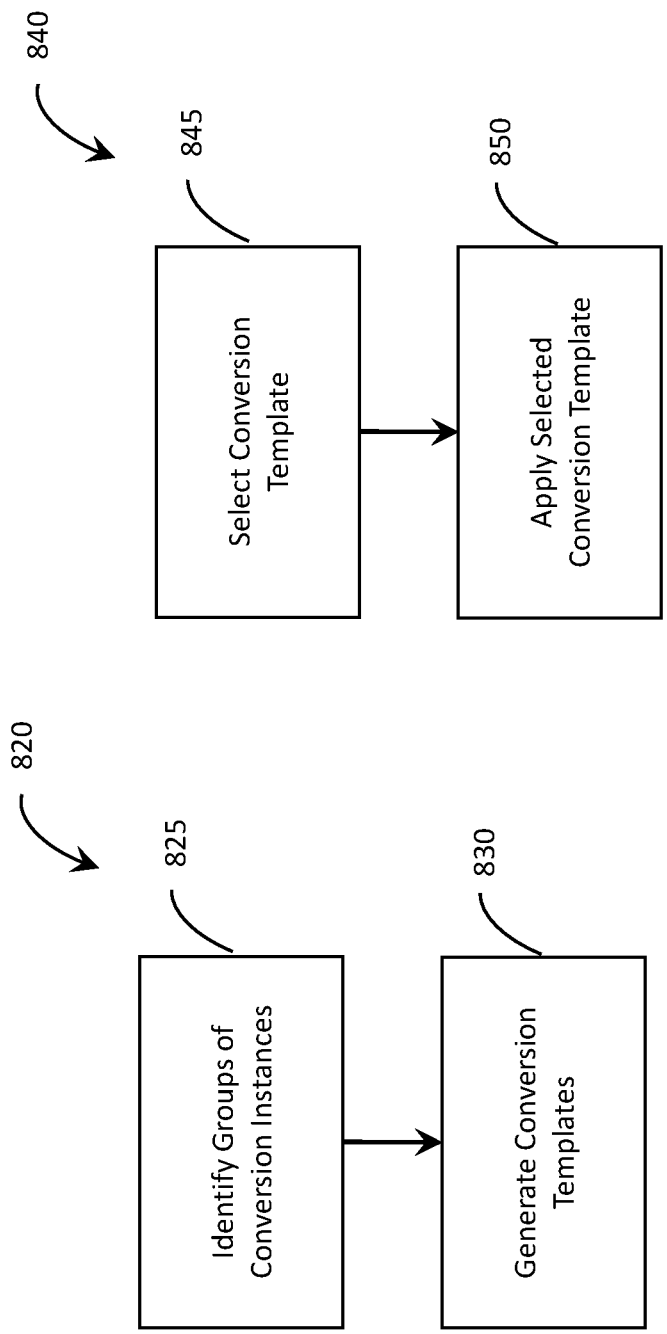
FIG. 8B shows an illustrative process 820 for generating conversion templates, in accordance with some embodiments.
FIG. 8C shows an illustrative process 840 for selecting and applying a conversion template, in accordance with some embodiments.

FIG. 8B shows an illustrative process 820 for generating conversion templates, in accordance with some embodiments. For instance, the process 820 may be used by the illustrative data conversion engine 100 the example of FIG. 1 to generate conversion templates based on the illustrative conversion instances 800-1, 800-2, . . . , 800-N in the example of FIG. 8A.

At act 825, the data conversion engine 100 may identify groups of conversion instances. For example, conversion instances having the same type may be placed into the same group. Additionally, or alternatively, conversion instances from the same industry or sub-industry may be placed into the same group.

It should be appreciated that aspects of the present disclosure are not limited to grouping conversion instances in any particular manner, or at all. In some embodiments, one or more clustering techniques may be used to analyze feature vectors of conversion instances, to detect potential patterns. A detected pattern may then be used to classify conversion instances.

At act 830, the data conversion engine 100 may generate a conversion template for each group of conversion instance(s) identified at act 825. For example, the conversion template may include one or more mappings of data structures that are common across all conversion instances in the group (or some threshold percentage of such conversion instances). Additionally, or alternatively, the conversion template may include one or more data queries that are common across all conversion instances in the group (or some threshold percentage of such conversion instances).

FIG. 8C shows an illustrative process 840 for selecting and applying a conversion template, in accordance with some embodiments. For instance, the process 840 may be used by the illustrative data conversion engine 100 the example of FIG. 1 to select and apply a conversion template for newly encountered source system 805-N' and target system 810-N' (not shown).

At act 845, the data conversion engine 100 may select a conversion template from a plurality of conversion templates. Some or all of these conversion templates may be generated using the illustrative process 820 in the example of FIG. 8B.

For example, the data conversion engine 100 may determine that the newly encountered source system 805-N' is an instance of a software application A, and the newly encountered target system 810-N' is an instance of a software application B. Accordingly, the data conversion engine 100 may select a conversion template for converting data from the software application A to the software application B.

Additionally, or alternatively, the data conversion engine 100 may determine that the newly encountered source system 805-N' and target system 810-N' are deployed in a certain industry or sub-industry, and may select a conversion template for that industry or sub-industry.

At act 850, the data conversion engine 100 may apply the conversion template selected at act 845 to the newly encountered source system 805-N' and target system 810-N'. For example, the data conversion engine 100 may apply one or more mappings of data structures and/or one or more data queries from the selected conversion template.

The inventors have recognized and appreciated that, while the selected conversion template may not be entirely accurate or comprehensive for the newly encountered source system 805-N' and target system 810-N', the process 840 may provide a significant improvement in performance. For instance, the selected conversion template may provide mappings for a significant percentage of target data structures in the target system 810-N', and the remaining target data structures may be matched using the illustrative process 460 in the example of FIG. 4C.

Additionally, or alternatively, the selected conversion template may provide data queries for a significant percentage of target data structures in the target system 810-N', and the remaining target data structures may be populated using the illustrative process 500 in the example of FIG. 5.

Additionally, or alternatively, one or more mappings and/or data queries from the selected conversion template may be tested and/or modified (e.g., as described above in connection with the example of FIG. 1) for the newly encountered source system 805-N' and target system 810-N'.

Illustrative configurations of various aspects of the present disclosure are provided below.

1.

Figure 9:
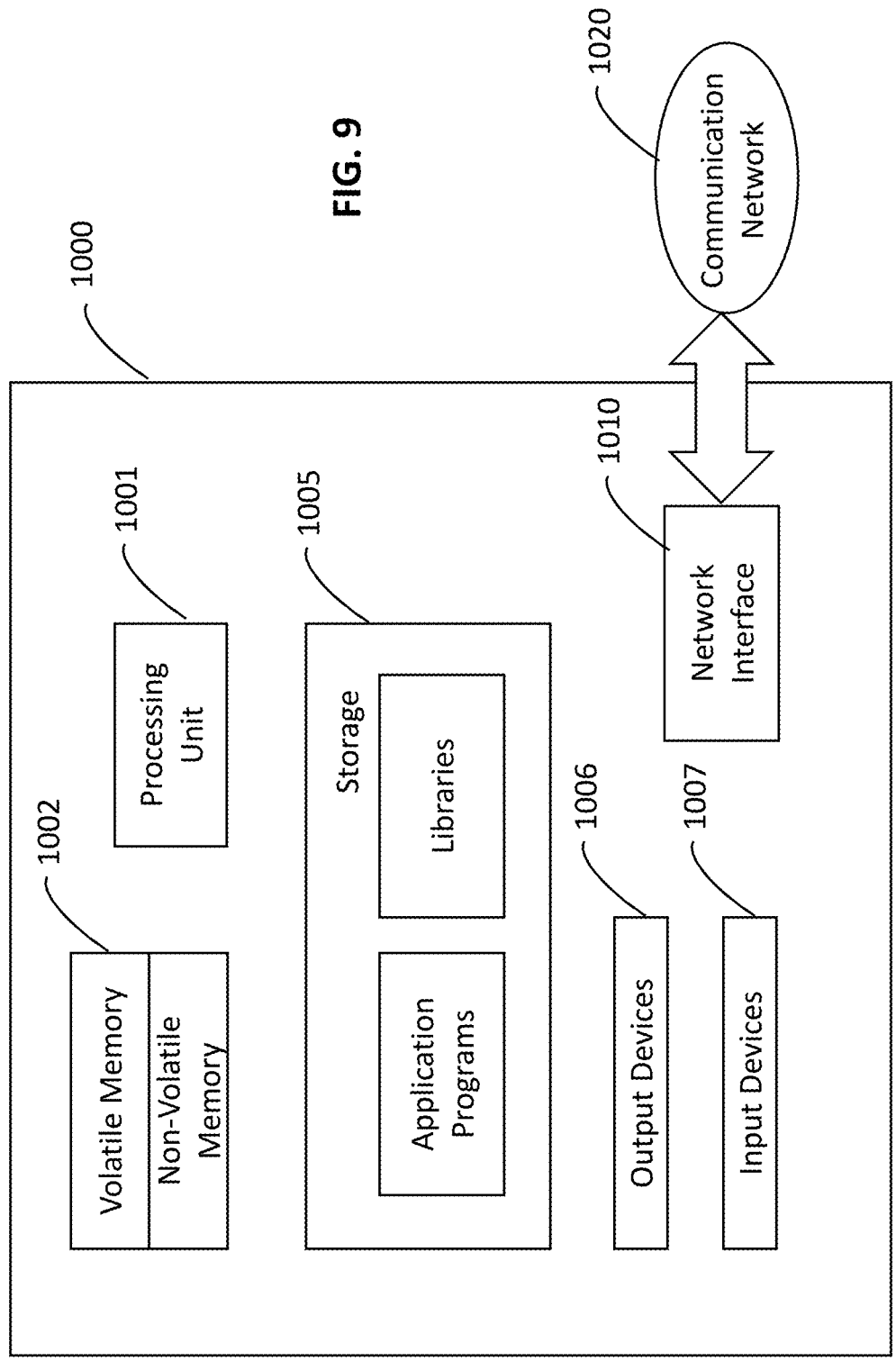
FIG. 9 shows, schematically, an illustrative computer 1000 on which any aspect of the present disclosure may be implemented.

FIG. 9 shows, schematically, an illustrative computer 1000 on which any aspect of the present disclosure may be implemented.

In the example of FIG. 9, the computer 1000 includes a processing unit 1001 having one or more computer hardware processors and one or more articles of manufacture that comprise at least one non-transitory computer-readable medium (e.g., memory 1002) that may include, for example, volatile and/or non-volatile memory. The memory 1002 may store one or more instructions to program the processing unit 1001 to perform any of the functions described herein. The computer 1000 may also include other types of non-transitory computer-readable media, such as storage 1005 (e.g., one or more disk drives) in addition to the memory 1002. The storage 1005 may also store one or more application programs and/or resources used by application programs (e.g., software libraries), which may be loaded into the memory 1002. To perform any of the illustrative functionalities described herein, processing unit 1001 may execute one or more processor-executable instructions stored in the one or more non-transitory computer-readable media (e.g., the memory 1002, the storage 1005, etc.), which may serve as non-transitory computer-readable media storing processor-executable instructions for execution by the processing unit 1001.

The computer 1000 may have one or more input devices and/or output devices, such as devices 1006 and 1007 illustrated in FIG. 9. These devices may be used, for instance, to present a user interface. Examples of output devices that may be used to provide a user interface include printers, display screens, and other devices for visual output, speakers and other devices for audible output, braille displays and other devices for haptic output, etc. Examples of input devices that may be used for a user interface include keyboards, pointing devices (e.g., mice, touch pads, and digitizing tablets), microphones, etc. For instance, the input devices 1007 may include a microphone for capturing audio signals, and the output devices 1006 may include a display screen for visually rendering, and/or a speaker for audibly rendering, recognized text.

In the example of FIG. 9, the computer 1000 also includes one or more network interfaces (e.g., network interface 1010) to enable communication via various networks (e.g., network 1020). Examples of networks include local area networks (e.g., an enterprise network), wide area networks (e.g., the Internet), etc. Such networks may be based on any suitable technology operating according to any suitable protocol, and may include wireless networks and/or wired networks (e.g., fiber optic networks).

Having thus described several aspects of at least one embodiment, it is to be appreciated that various alterations, modifications, and improvements will readily occur to those skilled in the art. Such alterations, modifications, and improvements are intended to be within the spirit and scope of the present disclosure. Accordingly, the foregoing descriptions and drawings are by way of example only.

The above-described embodiments of the present disclosure can be implemented in any of numerous ways. For example, the embodiments may be implemented using hardware, software, or a combination thereof. When implemented in software, the software code may be executed on any suitable processor or collection of processors, whether provided in a single computer or distributed among multiple computers.

Also, the various methods or processes outlined herein may be coded as software that is executable on one or more processors running any one of a variety of operating systems or platforms. Such software may be written using any of a number of suitable programming languages and/or programming tools, including scripting languages and/or scripting tools. In some instances, such software may be compiled as executable machine language code or intermediate code that is executed on a framework or virtual machine. Additionally, or alternatively, such software may be interpreted.

The techniques disclosed herein may be embodied as a non-transitory computer-readable medium (or multiple non-transitory computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer-readable media) encoded with one or more programs that, when executed on one or more processors, perform methods that implement the various embodiments of the present disclosure described above. The computer-readable medium or media may be portable, such that the program or programs stored thereon may be loaded onto one or more different computers or other processors to implement various aspects of the present disclosure as described above.

The terms "program" or "software" are used herein to refer to any type of computer code or set of computer-executable instructions that may be employed to program one or more processors to implement various aspects of the present disclosure as described above. Moreover, it should be appreciated that according to one aspect of this embodiment, one or more computer programs that, when executed, perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Program modules may include routines, programs, objects, components, data structures, etc. that perform particular tasks or implement particular abstract data types. Functionalities of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields to locations in a computer-readable medium, so that the locations convey how the fields are related. However, any suitable mechanism may be used to relate information in fields of a data structure, including through the use of pointers, tags, or other mechanisms that establish how the data elements are related.

Various features and aspects of the present disclosure may be used alone, in any combination of two or more, or in a variety of arrangements not specifically described in the foregoing, and are therefore not limited to the details and arrangement of components set forth in the foregoing description or illustrated in the drawings. For example, aspects described in one embodiment may be combined in any manner with aspects described in other embodiments.

Also, the techniques disclosed herein may be embodied as methods, of which examples have been provided. The acts performed as part of a method may be ordered in any suitable way. Accordingly, embodiments may be constructed in which acts are performed in an order different from illustrated, which may include performing some acts simultaneously, even though shown as sequential acts in illustrative embodiments.

Use of ordinal terms such as "first," "second," "third," etc. in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Also, the phraseology and terminology used herein is for the purpose of description and should not be regarded as limiting. The use of "including," "comprising," "having," "containing," "involving," "based on," "according to," "encoding," and variations thereof herein, is meant to encompass the items listed thereafter and equivalents thereof as well as additional items.

What is claimed is:

1. A computer-implemented method for data conversion from a source system to a target system, the source system comprising a plurality of source data structures, the target system comprising a target data structure, the method comprising acts of:
   for each source data structure of the plurality of source data structures, computing a respective conversion score between the source data structure and the target data structure; and
   matching, based on the conversion scores, the target data structure to a source data structure of the plurality of source data structures, wherein the act of computing a respective conversion score between the source data structure and the target data structure comprises acts of:
   matching a name of the source data structure to a first term in a data dictionary;
   matching a name of the target data structure to a second term in the data dictionary; and
   computing a sub-score based on the first term and the second term.

2. The method of claim 1, wherein:
   the act of matching the target data structure to a source data structure comprises:
   selecting, from the plurality of source data structures, a source data structure having a highest conversion score.

3. The method of claim 1, wherein:
   the source data structure includes a plurality of source data fields; and/or
   the target data structure includes a plurality of target data fields.

4. The method of claim 1, wherein:
   the conversion score between the source data structure and the target data structure is determined based on respective feature vectors of the source data structure and the target data structure; and
   each feature vector comprises a value selected from a group consisting of: a name, a description, a data type, a data size, a classification label, and a value indicative of a relationship with another data structure.

5. The method of claim 1, wherein:
   the sub-score is determined based on semantic similarity between the first term and the second term.

6. The method of claim 1, wherein:
   the act of matching a name of the source data structure to a first term in a data dictionary comprises acts of:
   tokenizing the name of the source data structure to obtain one or more first tokens; and
   matching the one or more first tokens to the first term in the data dictionary; and/or
   the act of matching a name of the target data structure to a second term in the data dictionary comprises acts of:
   tokenizing the name of the target data structure to obtain one or more second tokens; and matching the one or more second tokens to the second term in the data dictionary.

7. The method of claim 1, wherein:
the first and second terms are associated, respectively, with first and second entries in the data dictionary;
the data dictionary further comprises a third entry associated with a third term, the third entry storing an indication that the third term is related to the first term; and
the act of matching a name of the source data structure to a first term in the data dictionary comprises acts of:
matching the name of the source data structure to the third entry in the data dictionary; and
using the third entry to navigate to the first entry, thereby identifying the first term.

8. The method of claim 1, wherein:
the first and second terms are associated, respectively, with first and second entries in the data dictionary;
the data dictionary further comprises a fourth entry associated with a fourth term, the fourth entry storing an indication that the fourth term is related to the second term; and
the act of matching a name of the target data structure to a second term in a data dictionary comprises acts of:
matching the name of the target data structure to the fourth entry in the data dictionary; and
using the fourth entry to navigate to the second entry, thereby identifying the second term.

9. The method of claim 1, further comprising acts of:
accessing data from the matched source data structure; and
using the accessed data to prepare data to be loaded into the target data structure.

10. The method of claim 9, wherein:
the act of using the accessed data to prepare data to be loaded into the target data structure comprises:
transforming the accessed data according to one or more input specifications of the target system, thereby obtaining transformed data; and
using the transformed data to prepare data to be loaded into the target data structure.

11. The method of claim 10, wherein:
the one or more input specifications of the target system comprise:
an input specification relating to data content for the target data structure;
an input specification relating to data format for the target data structure; and/or
an input specification relating to one or more load constraints involving the target data structure.

12. The method of claim 9, further comprising acts of:
loading the prepared data into the target data structure; and
testing the target system after the prepared data has been loaded.

13. The method of claim 12, wherein:
the act of testing the target system comprises acts of:
using a selected downstream system to generate a first report based on data accessed from the source system;
using the selected downstream system to generate a second report based on data accessed from the target system; and
comparing the first and second reports.

14. The method of claim 12, wherein:
the prepared data comprises first source data to be loaded into the target data structure;
the matched source data structure comprises a first source data structure; and
the method further comprises acts of, in response to detecting an anomaly:
matching the target data structure to a second source data structure different from the first source data structure; and
using data accessed from the second source data structure to prepare second source data to be loaded into the target data structure.

15. The method of claim 1, wherein:
the target data structure comprises a first target data field and a second target data field;
the matched source data structure comprises:
a first source data field matched to the first target data field, and
a second source data field matched to the second target data field;
the first source data field is in a first data table in the source system;
the second source data field is in a second data table in the source system, the second data table being different from the first data table; and
the method further comprises an act of:
generating one or more queries for accessing the second data table from the first data table.

16. The method of claim 15, wherein:
the act of generating one or more queries for accessing the second data table from the first data table comprises acts of:
identifying a path from a first node to a second node in a graph; and
using the identified path to generate the one or more queries; and
each node in the path corresponds to a data table in the source system;
the first and second nodes correspond, respectively, to the first and second data tables;
each edge between two nodes in the graph represents a connection between data tables corresponding, respectively, to the two nodes.

17. The method of claim 16, wherein:
the act of identifying a path from a first node to a second node comprises an act of:
using one or more optimization techniques to identify a shortest path from the first node to the second node.

18. The method of claim 16, wherein:
each edge in the graph has an associated cost; and
the act of identifying a path from a first node to a second node comprises an act of:
using one or more optimization techniques to identify a least costly path from the first node to the second node.

19. The method of claim 1, wherein:
the source data structure comprises a first source data structure;
the target data structure comprises a first target data structure; and
the method further comprises acts of:
selecting, from a plurality of conversion templates, a conversion template for the source system and the target system; and
applying the conversion template to match a second target data structure in the target system to a second source data structure in the source system.

20. A system for data conversion from a source system to a target system, the source system comprising a plurality of source data structures, the target system comprising a target data structure, the system comprising:
at least one processor; and
at least one computer-readable storage medium having stored thereon instructions which, when executed, program the at least one processor to:
for each source data structure of the plurality of source data structures, compute a respective conversion score between the source data structure and the target data structure; and
match, based on the conversion scores, the target data structure to a source data structure of the plurality of source data structures, wherein the at least one processor is configured to compute a respective conversion score between the source data structure and the target data structure at least in part by:
matching a name of the source data structure to a first term in a data dictionary;
matching a name of the target data structure to a second term in the data dictionary; and
computing a sub-score based on the first term and the second term.

21. The system of claim 20, wherein:
the at least one processor is configured to match the target data structure to a source data structure at least in part by:
selecting, from the plurality of source data structures, a source data structure having a highest conversion score.

22. The system of claim 20, wherein:
the source data structure includes a plurality of source data fields; and/or
the target data structure includes a plurality of target data fields.

23. The system of claim 20, wherein:
the conversion score between the source data structure and the target data structure is determined based on respective feature vectors of the source data structure and the target data structure; and
each feature vector comprises a value selected from a group consisting of: a name, a description, a data type, a data size, a classification label, and a value indicative of a relationship with another data structure.

24. The system of claim 20, wherein:
the sub-score is determined based on semantic similarity between the first term and the second term.

25. The system of claim 20, wherein:
the at least one processor is configured to match a name of the source data structure to a first term in a data dictionary at least in part by:
tokenizing the name of the source data structure to obtain one or more first tokens; and
matching the one or more first tokens to the first term in the data dictionary; and/or
the at least one processor is configured to match a name of the target data structure to a second term in the data dictionary at least in part by:
tokenizing the name of the target data structure to obtain one or more second tokens; and
matching the one or more second tokens to the second term in the data dictionary.

26. The system of claim 20, wherein:
the first and second terms are associated, respectively, with first and second entries in the data dictionary;
the data dictionary further comprises a third entry associated with a third term, the third entry storing an indication that the third term is related to the first term; and
the at least one processor is configured to match a name of the source data structure to a first term in a data dictionary at least in part by:
matching the name of the source data structure to the third entry in the data dictionary; and
using the third entry to navigate to the first entry, thereby identifying the first term.

27. The system of claim 20, wherein:
the first and second terms are associated, respectively, with first and second entries in the data dictionary;
the data dictionary further comprises a fourth entry associated with a fourth term, the fourth entry storing an indication that the fourth term is related to the second term; and
the at least one processor is configured to match a name of the target data structure to a second term in the data dictionary at least in part by:
matching the name of the target data structure to the fourth entry in the data dictionary; and
using the fourth entry to navigate to the second entry, thereby identifying the second term.

28. The system of claim 20, wherein the at least one processor is further configured to:
access data from the matched source data structure; and
use the accessed data to prepare data to be loaded into the target data structure.

29. The system of claim 28, wherein:
the at least one processor is configure to use the accessed data to prepare data to be loaded into the target data structure at least in part by:
transforming the accessed data according to one or more input specifications of the target system, thereby obtaining transformed data; and
using the transformed data to prepare data to be loaded into the target data structure.

30. The system of claim 29, wherein:
the one or more input specifications of the target system comprise:
an input specification relating to data content for the target data structure;
an input specification relating to data format for the target data structure; and/or
an input specification relating to one or more load constraints involving the target data structure.

31. The system of claim 28, wherein the at least one processor is further configured to:
load the prepared data into the target data structure; and
test the target system after the prepared data has been loaded.

32. The system of claim 31, wherein:
the at least one processor is further configured to test the target system at least in part by:
using a selected downstream system to generate a first report based on data accessed from the source system;
using the selected downstream system to generate a second report based on data accessed from the target system; and
comparing the first and second reports.

33. The system of claim 31, wherein:
the prepared data comprises first source data to be loaded into the target data structure;
the matched source data structure comprises a first source data structure; and the at least one processor is further configured to, in response to detecting an anomaly:
  match the target data structure to a second source data structure different from the first source data structure; and
  use data accessed from the second source data structure to prepare second source data to be loaded into the target data structure.

34. The system of claim 20, wherein:
the target data structure comprises a first target data field and a second target data field;
the matched source data structure comprises:
  a first source data field matched to the first target data field, and
  a second source data field matched to the second target data field;
the first source data field is in a first data table in the source system;
the second source data field is in a second data table in the source system, the second data table being different from the first data table; and
the at least one processor is further configured to:
  generate one or more queries for accessing the second data table from the first data table.

35. The system of claim 34, wherein:
the at least one processor is configured to generate one or more queries for accessing the second data table from the first data table at least in part by:
  identifying a path from a first node to a second node in a graph; and
  using the identified path to generate the one or more queries; and
each node in the path corresponds to a data table in the source system;
the first and second nodes correspond, respectively, to the first and second data tables;
each edge between two nodes in the graph represents a connection between data tables corresponding, respectively, to the two nodes.

36. The system of claim 35, wherein:
the at least one processor is configured to identify a path from a first node to a second node at least in part by:
  using one or more optimization techniques to identify a shortest path from the first node to the second node.

37. The system of claim 35, wherein:
each edge in the graph has an associated cost; and
the at least one processor is configured to identify a path from a first node to a second node at least in part by:
  using one or more optimization techniques to identify a least costly path from the first node to the second node.

38. The system of claim 20, wherein:
the source data structure comprises a first source data structure;
the target data structure comprises a first target data structure; and
the at least one processor is further configured to:
  select, from a plurality of conversion templates, a conversion template for the source system and the target system; and
  apply the conversion template to match a second target data structure in the target system to a second source data structure in the source system.

39. At least one non-transitory computer-readable storage medium having stored thereon instructions which, when executed, program at least one processor to perform a method for data conversion from a source system to a target system, the source system comprising a plurality of source data structures, the target system comprising a target data structure, the method comprising acts of:
  for each source data structure of the plurality of source data structures, computing a respective conversion score between the source data structure and the target data structure; and
  matching, based on the conversion scores, the target data structure to a source data structure of the plurality of source data structures, wherein the act of computing a respective conversion score between the source data structure and the target data structure comprises acts of:
    matching a name of the source data structure to a first term in a data dictionary;
    matching a name of the target data structure to a second term in the data dictionary; and
    computing a sub-score based on the first term and the second term.

40. The at least one non-transitory computer-readable storage medium of claim 39, wherein:
the act of matching the target data structure to a source data structure comprises:
  selecting, from the plurality of source data structures, a source data structure having a highest conversion score.

41. The at least one non-transitory computer-readable storage medium of claim 39, wherein:
the source data structure includes a plurality of source data fields; and/or
the target data structure includes a plurality of target data fields.

42. The at least one non-transitory computer-readable storage medium of claim 39, wherein:
the conversion score between the source data structure and the target data structure is determined based on respective feature vectors of the source data structure and the target data structure; and
each feature vector comprises a value selected from a group consisting of: a name, a description, a data type, a data size, a classification label, and a value indicative of a relationship with another data structure.

43. The at least one non-transitory computer-readable storage medium of claim 39, wherein:
the sub-score is determined based on semantic similarity between the first term and the second term.

44. The at least one non-transitory computer-readable storage medium of claim 39 wherein:
the act of matching a name of the source data structure to a first term in a data dictionary comprises acts of:
  tokenizing the name of the source data structure to obtain one or more first tokens; and
  matching the one or more first tokens to the first term in the data dictionary; and/or
the act of matching a name of the target data structure to a second term in the data dictionary comprises acts of:
  tokenizing the name of the target data structure to obtain one or more second tokens; and
  matching the one or more second tokens to the second term in the data dictionary.

45. The at least one non-transitory computer-readable storage medium of claim 39, wherein:
the first and second terms are associated, respectively, with first and second entries in the data dictionary;
the data dictionary further comprises a third entry associated with a third term, the third entry storing an indication that the third term is related to the first term; and the act of matching a name of the source data structure to a first term in a data dictionary comprises acts of:
  matching the name of the source data structure to the third entry in the data dictionary; and
  using the third entry to navigate to the first entry, thereby identifying the first term.

46. The at least one non-transitory computer-readable storage medium of claim 39, wherein:
  the first and second terms are associated, respectively, with first and second entries in the data dictionary;
  the data dictionary further comprises a fourth entry associated with a fourth term, the fourth entry storing an indication that the fourth term is related to the second term; and
  the act of matching a name of the target data structure to a second term in the data dictionary comprises acts of:
    matching the name of the target data structure to the fourth entry in the data dictionary; and
    using the fourth entry to navigate to the second entry, thereby identifying the second term.

47. The at least one non-transitory computer-readable storage medium of claim 39, wherein the method further comprises acts of:
  accessing data from the matched source data structure; and
  using the accessed data to prepare data to be loaded into the target data structure.

48. The at least one non-transitory computer-readable storage medium of claim 47, wherein:
  the act of using the accessed data to prepare data to be loaded into the target data structure comprises:
    transforming the accessed data according to one or more input specifications of the target system, thereby obtaining transformed data; and
    using the transformed data to prepare data to be loaded into the target data structure.

49. The at least one non-transitory computer-readable storage medium of claim 48, wherein:
  the one or more input specifications of the target system comprise:
    an input specification relating to data content for the target data structure;
    an input specification relating to data format for the target data structure; and/or
    an input specification relating to one or more load constraints involving the target data structure.

50. The at least one non-transitory computer-readable storage medium of claim 48, wherein the method further comprises acts of:
  loading the prepared data into the target data structure; and
  testing the target system after the prepared data has been loaded.

51. The at least one non-transitory computer-readable storage medium of claim 50, wherein:
  the act of testing the target system comprises acts of:
    using a selected downstream system to generate a first report based on data accessed from the source system;
    using the selected downstream system to generate a second report based on data accessed from the target system; and
    comparing the first and second reports.

52. The at least one non-transitory computer-readable storage medium of claim 50, wherein:
  the prepared data comprises first source data to be loaded into the target data structure;
  the matched source data structure comprises a first source data structure; and
  the method further comprises acts of, in response to detecting an anomaly:
    matching the target data structure to a second source data structure different from the first source data structure; and
    using data accessed from the second source data structure to prepare second source data to be loaded into the target data structure.

53. The at least one non-transitory computer-readable storage medium of claim 39, wherein:
  the target data structure comprises a first target data field and a second target data field;
  the matched source data structure comprises:
    a first source data field matched to the first target data field, and
    a second source data field matched to the second target data field;
  the first source data field is in a first data table in the source system;
  the second source data field is in a second data table in the source system, the second data table being different from the first data table; and
  the method further comprises an act of:
    generating one or more queries for accessing the second data table from the first data table.

54. The at least one non-transitory computer-readable storage medium of claim 53, wherein:
  the act of generating one or more queries for accessing the second data table from the first data table comprises acts of:
    identifying a path from a first node to a second node in a graph; and
    using the identified path to generate the one or more queries; and
  each node in the path corresponds to a data table in the source system;
  the first and second nodes correspond, respectively, to the first and second data tables;
  each edge between two nodes in the graph represents a connection between data tables corresponding, respectively, to the two nodes.

55. The at least one non-transitory computer-readable storage medium of claim 54, wherein:
  the act of identifying a path from a first node to a second node comprises an act of:
    using one or more optimization techniques to identify a shortest path from the first node to the second node.

56. The at least one non-transitory computer-readable storage medium of claim 54, wherein:
  each edge in the graph has an associated cost; and
  the act of identifying a path from a first node to a second node comprises an act of:
    using one or more optimization techniques to identify a least costly path from the first node to the second node.

57. The at least one non-transitory computer-readable storage medium of claim 39, wherein:
  the source data structure comprises a first source data structure;
  the target data structure comprises a first target data structure; and
  the method further comprises acts of:
    selecting, from a plurality of conversion templates, a conversion template for the source system and the target system; and applying the conversion template to match a second target data structure in the target system to a second source data structure in the source system.

* * * * *